United States Patent [19]

Walker

[11] 4,375,474
[45] Mar. 1, 1983

[54] DIOXALANE CONTAINING IMIDAZOLE COMPOUNDS, COMPOSITIONS AND USE

[75] Inventor: Keith A. M. Walker, Los Altos Hills, Calif.

[73] Assignee: Syntex (U.S.A.) Inc., Palo Alto, Calif.

[21] Appl. No.: 347,832

[22] Filed: Feb. 11, 1982

[51] Int. Cl.³ ............... C07D 405/06; A61K 31/415
[52] U.S. Cl. ............................. 424/273 R; 548/336
[58] Field of Search .................. 548/336; 424/273 R

[56] References Cited

U.S. PATENT DOCUMENTS

| 3,936,470 | 2/1976 | Heeres | 548/336 |
| 4,101,664 | 7/1978 | Heeres | 548/336 |
| 4,101,665 | 7/1978 | Heeres | 548/331 |
| 4,101,666 | 7/1978 | Heeres | 548/331 |
| 4,144,346 | 3/1979 | Heeres et al. | 548/336 |
| 4,321,272 | 3/1982 | Walker | 548/336 |

OTHER PUBLICATIONS

European Patent Application, 269, (4/15/81).

*Primary Examiner*—Robert W. Ramsuer
*Attorney, Agent, or Firm*—Annette M. Moore; Tom M. Moran

[57] ABSTRACT

Compounds useful as antifungal, antibacterial and antiprotozoal agents are represented by the formula:

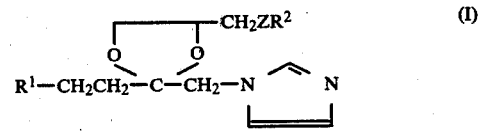

wherein:
  Z is oxygen or sulfur;
  $R^1$ is phenyl optionally substituted with one or more substituents selected from the group consisting of halo, lower alkyl of one to four carbon atoms, lower alkoxy of one to four carbon atoms and trifluoromethyl;
  $R^2$ is phenyl or benzyl wherein the phenyl ring of $R^2$ is optionally substituted by one or more substituents selected from the group consisting of halo, lower alkyl of one to four carbon atoms, lower alkoxy of one to four carbon atoms and trifluoromethyl; or by a phenyl optionally substituted by halo, lower alkyl of one to four carbon atoms, lower alkoxy of one to four carbon atoms or trifluoromethyl; and
  the antimicrobial acid addition salts thereof.

56 Claims, No Drawings

DIOXALANE CONTAINING IMIDAZOLE COMPOUNDS, COMPOSITIONS AND USE

BACKGROUND OF THE INVENTION

1. Field of the Invention

This invention relates to derivatives of cyclic ketals of N-alkylimidazoles and the antimicrobial acid addition salts thereof, which are useful as antimicrobial agents. The invention also relates to compositions containing an effective amount of at least one of the compounds in combination with a suitable excipient, the composition being useful for combatting fungi, bacteria and protozoa. The invention also relates to novel intermediates and to a process for making the compounds of the invention.

2. Related Disclosures

Compounds of the following formula are known $$R^1-\underset{\underset{O\diagdown\diagup O}{|}}{C}-CH_2-N\underset{\diagdown=\diagup}{\frown}N \quad \text{with } CH_2ZR^2$$

wherein:
R[1] is, i.a., phenyl optionally substituted with one or more substituents selected from the group consisting of halo, alkyl, alkoxy, nitro, and cyano;
R[2] is, i.a., phenyl or benzyl wherein the phenyl ring of R[2] is optionally substituted by one or more substituents selected from the group consisting of halo, alkyl, alkoxy, and phenyl;
Z is oxygen or sulfur; and when Z is oxygen R[2] may be hydrogen. See U.S. Pat. Nos. 3,936,470, 4,101,664, 4,101,665, 4,101,666 and 4,144,346, and Great Britain Pat. No. 1,528,639.

SUMMARY OF THE INVENTION

The first aspect of the invention is a group of compounds of the formula $$R^1-CH_2CH_2-\underset{\underset{O\diagdown\diagup O}{|}}{C}-CH_2-N\underset{\diagdown=\diagup}{\frown}N \quad \text{with } CH_2ZR^2 \quad (I)$$

wherein:
Z is oxygen, or sulfur;
R[1] is phenyl optionally substituted by one or more substituents selected from the group consisting of halo, lower alkyl, lower alkoxy and trifluoromethyl;
R[2] is phenyl or benzyl wherein the phenyl ring of R[2] is optionally substituted by one or more substituents selected from the group consisting of halo, lower alkyl, lower alkoxy and trifluoromethyl; or by a phenyl optionally substituted by halo, lower alkyl, lower alkoxy or trifluoromethyl; and
the antimicrobial acid addition salts thereof.

Another aspect of the invention is a composition containing at least one compound of formula (I) in admixture with an acceptable carrier useful in combatting fungi, bacteria and protozoa.

Another aspect of the invention is a method of combatting fungi, bacteria and protozoa by administering at least one compound of formula (I).

A further aspect of the invention is novel intermediates useful in preparing the compounds of formula (I) and of the formulas $$R^1-CH_2CH_2-\underset{\underset{O\diagdown\diagup O}{|}}{C}-CH_2-N\underset{\diagdown=\diagup}{\frown}N \quad \text{with } CH_2OH \quad (IIa)$$

and $$R^1-CH_2CH_2-\underset{\underset{O\diagdown\diagup O}{|}}{C}-CH_2-N\underset{\diagdown=\diagup}{\frown}N \quad \text{with } CH_2W \quad (IIb)$$

wherein:
R[1] is as defined above and W is a leaving group such as halo or sulfonate, e.g., mesylate and the like, and the acid addition salts thereof; and $$R^1-CH_2CH_2-\underset{\underset{O\diagdown\diagup O}{|}}{C}-CH_2-Y \quad \text{with } CH_2ZR^2 \quad (III)$$

wherein:
R[1], R[2] and Z are as defined above and Y is a leaving group such as halo, e.g., chloro, bromo or iodo, or a sulfonate ester.

Yet another aspect of the invention is a process for preparing compounds of formula (I) by: (1) reacting compounds of formula (IIa) with R[2]Y wherein Y is a leaving group, as defined above, or (2) reacting a compound of formula (IIb) with R[2]OH, wherein R[2] is optionally substituted phenyl or with R[2]SH wherein R[2] is optionally substituted phenyl or optionally substituted benzyl, or (3) reacting compounds of formula (III) with imidazole and/or an imidazole salt, or (4) ketalizing a compound of the formula $$R^1-CH_2CH_2-\underset{\underset{O}{\|}}{C}-CH_2-N\underset{\diagdown=\diagup}{\frown}N \quad (V)$$

with an ethylene glycol of the formula $$\underset{\underset{OH}{|}}{CH_2}\underset{\underset{OH}{|}}{CH}CH_2ZR^2$$

Detailed Description of the Invention and Preferred Embodiments

The broadest aspect of the present invention is a group of compounds of the formula

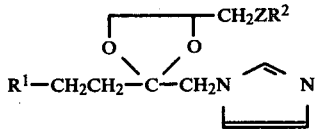

(I)

wherein:
  Z is oxygen or sulfur;
  $R^1$ is phenyl optionally substituted with one or more substituents selected from the group consisting of halo, lower alkyl, lower alkoxy and trifluoromethyl;
  $R^2$ is phenyl or benzyl wherein the phenyl ring of $R^2$ is optionally substituted by one or more substituents selected from the group consisting of halo, lower alkyl, lower alkoxy and trifluoromethyl; or a phenyl optionally substituted by halo, lower alkyl, lower alkoxy or trifluoromethyl; and
  the antimicrobial acid addition salts thereof.

As used in the specification and the appended claims, unless specified to the contrary, the following terms have the meaning indicated. The term "lower alkyl" refers to a straight or branched chain monovalent substituent consisting solely of carbon and hydrogen, containing no unsaturation, and having from one to four carbon atoms. Examples of lower alkyl groups are methyl, ethyl, n-propyl, i-propyl, n-butyl, i-butyl, s-butyl and t-butyl. The term "lower alkoxy" refers to a straight or branched chain monovalent substituent consisting solely of carbon, hydrogen and oxygen and of the formula "lower alkyl-O-" wherein "lower alkyl" is as defined above. Examples of lower alkoxy groups are methoxy, ethoxy, n-propoxy, i-propoxy, n-butoxy, i-butoxy, s-butoxy and t-butoxy. The term "halo" refers to fluoro, chloro and bromo. "Antimicrobial acid addition salts" of the subject bases refers to those salts which possess the antimicrobial properties of the free bases and which are neither biologically nor otherwise undesirable, formed with, for example, inorganic acids such as hydrochloric acid, hydrobromic acid, sulfuric acid, nitric acid or phosphoric acid; or organic acids such as acetic acid, propionic acid, glycolic acid, lactic acid, pyruvic acid, oxalic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. It is also understood, for purposes of this invention, that the phenyl ring of $R^1$ and the phenyl ring of $R^2$ cannot be substituted with three or more adjacent branched alkyl, branched alkoxy and/or trifluoromethyl groups.

The compounds of formula (I) can be considered to consist of two subclasses, those of formulas (Ia) and (Ib) shown below:

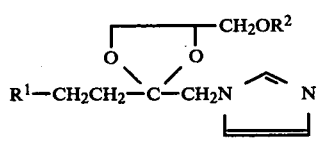

(Ia)

and

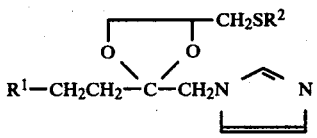

(Ib)

wherein $R^1$ and $R^2$ are as defined above.

One preferred subgenus of compounds of formulas (Ia) and (Ib) is that wherein $R^1$ is substituted phenyl. Within this group, preferred compounds are those wherein $R^1$ is substituted by one or two substituents selected from the group consisting of halo, lower alkyl or lower alkoxy. More preferred compounds are those wherein $R^1$ is substituted in the 4-position with methoxy, halo or lower alkyl, Especially preferred is 4-methoxy, 4-chloro or 4-methyl substitution.

Another preferred subgenus of compounds of formulas (Ia) and (Ib) is that wherein the phenyl group of $R^2$ is unsubstituted or is substituted by a single substituent selected from the group consisting of halo, lower alkyl, lower alkoxy or phenyl, or by two substituents selected from the group consisting of halo, methyl or methoxy or by three substituents which are each chloro or each methyl. When the substituents are halo, chloro is preferred.

Within the above preferred subgenus, a more preferred group of compounds is those wherein
  (a) Z is oxygen and $R^2$ is 4-biphenyl or phenyl substituted in the 2 and/or 4 position and optionally in the 3, 5 or 6 position with identical substituents which is chloro or methyl;
  (b) Z is sulfur and $R^2$ is phenyl, 2-chlorophenyl, 3-chlorophenyl or 4-chlorophenyl; or
  (c) Z is oxygen or sulfur and $R^2$ is benzyl, 2-methoxybenzyl, 4-methoxybenzyl or benzyl substituted with one or two identical substituents which is chloro or methyl in the 2 and/or 4 position and optionally in the 3,5 or 6 position.

In all of the above preferred groups, cis isomers are preferred over the trans isomers (see infra).

FORMULATIONS AND ADMINISTRATIONS

The subject compounds of formula (I) exhibit antifungal, antibacterial and antiprotozoal activity. For example, compounds of the present invention exhibit antifungal activity against human and animal pathogens such as
  Microsporum audouini,
  Microsporum gypseum,
  Microsporum gypseum-canis,
  Epidermophyton floccosum,
  Trichophyton mentagrophytes,
  Trichophyton rubrum
  Trichophyton tonsurans
  Candida albicans, and
  Cryptococcus neoformans.

The compounds of the present invention also exhibit antifungal activity against the following fungi primarily of agricultural significance:
  Aspergillus flavus,
  Cladosporium herbarum,
  Fusarium graminearum,
  Penicillium notatum,
  Aspergillus niger,
  Penicillium oxalicum,
  Penicillium spinulosum, and
  Pithomyces chartarum.

In addition, the compounds of the present invention exhibit antibacterial activity against human and animal pathogens, such as Staphylococcus aureus,
Streptococcus faecalis,
Corynebacterium acnes,
Erysipelothrix insidiosa,
Escherischia coli,
Proteus vulgaris,
Salmonella choleraesuis,
Pasterurella multocida, and
Pseudomonas aeruginosa.

Moreover, the compounds of the present invention exhibit antiprotozoal activity against protozoa such as Trichomonas vaginalis.

In general, the subject compounds of the instant invention exhibit a low level of toxicity. Moreover, these compounds demonstrate good solubility in the stratum corneum. Since dermatophyte (i.e., parasitic fungal) infections are usually localized in the dead tissue of the stratum corneum, solubility of antifungal agents in this tissue significantly enhances their effectiveness. Furthermore, the compounds of the instant invention attain high blood serum levels when administered orally or parenterally and are particularly useful in the treatment of systemic fungal infections.

In view of the aforementioned activities, the subject compounds are found to be useful antimicrobials, having not only pharmaceutical but also agricultural and industrial application.

Accordingly, a further aspect of the present invention relates to compositions for pharmaceutical, agricultural, and industrial use, which compositions comprise the subject compounds of formula (I) in combination with a suitable carrier. A still further aspect of the present invention relates to methods of inhibiting the growth of fungi, bacteria and protozoa by applying to a host object containing, or subject to attack by, fungi, bacteria or protozoa, an effective amount of a compound of the present invention or a suitable composition containing same.

In pharmaceutical applications, compositions may be solid, semi-solid or liquid in form such as tablets, capsules, powders, suppositories, liquid solutions, suspensions, creams, lotions, ointments and the like. Pharmaceutically acceptable non-toxic carriers, or excipients normally employed for solid formulations include tricalcium phosphate, calcium carbonate, kaolin, bentonite, talcum, gelatin, lactose, starch and the like; for semi-solid formulations there may be mentioned, for example, polyalkylene glycols, vaseline and other cream bases; for liquid formulations there may be mentioned, for example, water, oils of vegetable origin and low boiling solvents such as isopropanol, hydrogenated naphthalenes and the like. The pharmaceutical compositions containing the compounds of the present invention may be subjected to conventional pharmaceutical expedients such as sterilization and can contain conventional pharmaceutical excipients such as preservatives, stabilizing agents, emulsifying agents, salts for the adjustment of osmotic pressure and buffers. The compositions may also contain other therapeutically active materials. In pharmaceutical applications, the subject compounds and compositions may be administered to humans and animals by conventional methods, e.g., topically, orally, parenterally and the like. Parenteral administration includes intramuscular as well as subcutaneous and intravenous administration. Intravenous injection of imidazole-type antifungals has been demonstrated to be effective in the treatment of systemic mycoses (see for example, Drugs, 9, pp. 419–420, 1975, which describes the intravenous administration of miconazole, i.e., 1-[2,4-dichloro-$\beta$-(2',4'-dichlorobenzyloxy)phenethyl]imidazole nitrate, to patients with systemic candidiasis).

The pharmaceutical compositions hereof typically comprise one or more subject compounds of Formula (I) and a pharmaceutically acceptable, non-toxic carrier, and are preferably formulated in unit dosage form to facilitate administration (unit dosage being the amount of active ingredient administered on one occasion).

In general, for systemic (e.g., oral or parenteral) administration it is expedient to administer the active ingredient in amounts between about 0.1 and 50 mg./kg. body weight per day, preferably between about 0.5 and 20 mg./kg. body weight per day, preferably distributed over several applications (e.g., in 3 individual doses) in order to achieve most effective results. For localized (e.g., topical) administration, however, proportionately less of the active ingredient is required.

For systemic administration the therapeutically effective amount of active compound can vary from 1 percent weight (%w) to 99%w or more of the active compound based on the total formulation and about 99%w to 1%w of excipient. Preferably the active compound is present at a level of 20%w–80%w. For topical application the therapeutically effective amount of active compound can range from 0.01%w to 20%w, preferably from 0.1%w to 5%w based on total formulation.

The exact regimen for pharmaceutical administration of the compounds and compositions disclosed herein will necessarily be dependent upon the needs of the individual subject being treated, the type of treatment, e.g., whether preventative or curative, the type of organism involved and, of course, the judgment of the attending practitioner.

In agricultural applications, the subject compounds may be applied directly to plants (e.g., seeds, foilage) or to soil. For example, compounds of the present invention may be applied to seeds alone or in admixture with a powdered solid carrier. Typical powdered carriers are the various mineral silicates, e.g., mica, talc, pyrophyllite, and clays. The subject compounds may also be applied to the seeds in admixture with a conventional surface-active wetting agent with or without additional solid carrier. Surface-active wetting agents that can be used are any of the conventional anionic, non-anionic or cationic types. As a soil treatment for fungi and the like, the subject compounds can be applied as a dust in admixture with sand, soil or a powdered solid carrier such as a mineral silicate with or without additional surface-active agent, or the subject compounds can be applied as an aqueous spray optionally containing a surface-active dispersing agent and a powdered solid carrier. As a foliage treatment, the subject compounds may be applied to growing plants as an aqueous spray which contains a surface-active dispersing agent with or without a powdered solid carrier and hydrocarbon solvents. The effective amount of active compound based on total formulation for agricultural use may vary from 0.0001%w to 90%w depending on use.

In industrial applications, the subject compounds may be used to control bacteria and fungi by contacting the pathogens with the compounds in any known manner. Materials capable of supporting bacteria and fungi may be protected by contacting, mixing or impregnating these materials with the subject compounds. In order to increase their effect, the subject compounds may be combined with other pesticidal control agents such as fungicides, bactericides, insecticides, miticides and the like. A particularly important industrial/agricultural use for the subject compounds of the present invention is as a food preservative against bacteria and fungi which cause deterioration and spoilage of foods.

PROCESS OF THE INVENTION

Compounds of the formula (I) may be prepared by forming an ether or thioether from a suitable alcohol of formula (IIa)

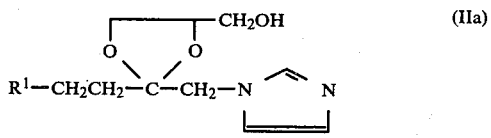

wherein:

$R^1$ is as defined above.

The above compounds of formula (IIa) are prepared as depicted in the following reaction sequences.

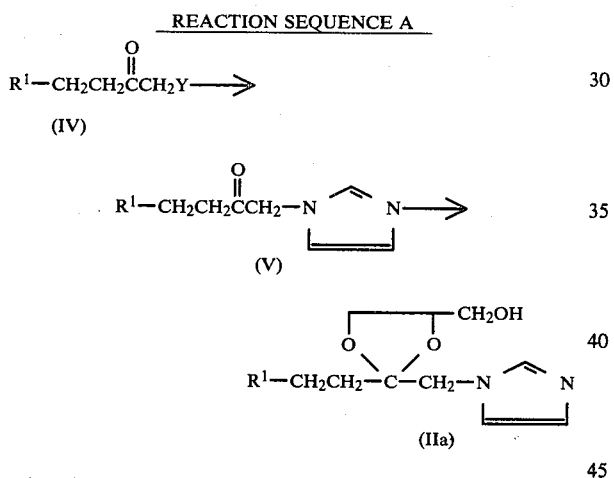

wherein:

$R^1$ and Y are as previously defined.

(a) The halo ketones of formula (IV) are generally known or are readily prepared using the methods disclosed in U.S. Pat. No. 4,078,071. The halo ketones are also conveniently prepared by oxidizing the corresponding halo alcohols, e.g., with Jones reagent. The halo alcohols are prepared by the method described in J. Med. Chem. 21:840, 1978 and J. Amer. Chem. Soc. 52:1164, 1930.

(b) The imidazole ketones of formula (V) are prepared according to the methods disclosed in U.S. Pat. No. 4,078,071, in particular by the method disclosed in reaction scheme B of that patent.

Compounds of formula (V) may also be prepared by oxidizing the alcohols of formula (VI)

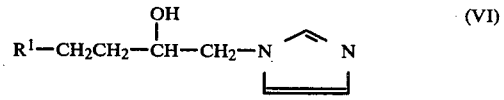

wherein:

$R^1$ is as defined above, by the method described in J. Org. Chem. 44(23):4148, 1979. Dimethyl sulfoxide is reacted with oxalyl chloride at $-100°$ to $-60°$ C. The intermediate formed is reacted with the alcohol of formula (VI) to form an alkoxy sulfonium salt which is converted to the ketone of formula (V) upon addition of triethylamine.

(c) Compounds of formula (V) are ketalized by treatment of the ketone (or an acid addition salt thereof) with glycerol in the presence of 1.02 molar equivalents to 2 molar equivalents of an acid or a Lewis acid, e.g., p-toluenesulfonic acid, perchloric acid, fuming sulfuric acid, boron trifluoride, zinc chloride and the like. A sulfonic acid, particularly p-toluenesulfonic acid is most preferred. When the acid addition salt of compounds of formula (V) is used only a catalytic amount of the acid or Lewis acid is required. The reaction is generally carried out using from 1 to 10 moles, preferably from 1 to 5 moles of glycerol relative to one mole of the ketone. Water is preferably removed as an azeotrope with a solvent, for example, a hydrocarbon such as cyclohexane or an aromatic hydrocarbon such as benzene or toluene, at a temperature sufficient to effect such azeotropic removal, e.g., from about 75° to about 150° C.

Compounds of formula (IIa) are also prepared as shown in the following reaction sequence.

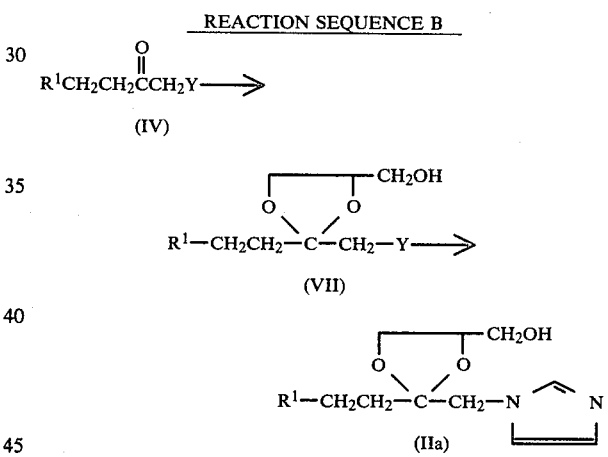

wherein:

$R^1$ and Y are as previously defined.

(d) The halo ketones of formula (IV) are ketalized to compounds of formula (VII) under similar reaction conditions as is described in (c) above except that only a catalytic amount of acid, e.g., about 0.01 to about 0.2 molar equivalents is used.

(e) The imidazole ketals of formula (IIa) are prepared by reacting the compounds of formula (VII) with imidazole and/or an imidazole salt, preferably an alkali metal salt, e.g., the sodium salt of imidazole in an inert organic solvent such as dimethylformamide, dimethylacetamide, hexamethylphosphoramide, tetrahydrofuran and the like at a temperature between 20° C. and 165° C. optionally in the presence of an alkali metal iodide such as sodium or potassium iodide. The reaction is generally carried out using from 1 to 5 moles of imidazole and/or 1 to 2 moles of the metal salt thereof relative to one mole of the compound of formula (VII).

The ketone of formula (IV) may also be ketalized to compounds of formulas (VII) or (III) and the ketone of formula (V) (supra) may also be ketalized to compounds of formulas (I) or (IIa) by the method described in Synthesis, 23, 1974. A ketone of formula (IV) or formula (V) is reacted with glycerol or an appropriately substituted ethylene glycol in a molar ratio of about 1:1 in an excess of a simple alcohol, for example, methanol, ethanol, n-butanol or benzyl alcohol in the presence of an appropriate amount (as described above) of an acid or a Lewis acid, e.g., p-toluenesulfonic acid, boron trifluoride, tin (IV) chloride and the like to form the cyclic ketal.

The cyclic ketals may also be prepared by other methods known in the art, such as by exchange with the ketal of a low boiling ketone.

The compounds of formula (IIa) are converted to the final products of formula (I) wherein Z is O and $R^2$ is substituted or unsubstituted benzyl by O-alkylation with the appropriate $R^2Y$ wherein Y is a leaving group such as halide (chloride, bromide or iodide) or sulfonate ester (e.g., p-toluenesulfonate or methanesulfonate).

The alkylation is carried out by converting the hydroxy group of the compound of formula (IIa) to its alkali metal salt by treatment with a strong base such as, for example, an alkali metal hydride such as sodium hydride, an alkali metal amide such as sodium amide or potassium amide, and the like. This is preferably done in an inert organic solvent such as, for example, dimethylformamide, hexamethylphosphoramide, dimethylsulfoxide, tetrahydrofuran, and the like. The alkali metal salt is then contacted with the $R^2Y$, preferably in the same solvent system, at a temperature between about 0° and 100° C., most preferably between about 25° and 85° C.

Compounds of formula (I) wherein $R^2$ is substituted or unsubstituted phenyl (i.e., phenolic ethers or thioethers) may be prepared from the compounds of formula (IIb) by a two-step sequence involving conversion of the hydroxy group of compounds of formula (IIa) to a suitable leaving group such as a halide (e.g., chloride, bromide or iodide) or a sulfonate ester (e.g., methanesulfonate or p-toluenesulfonate), i.e. a compound of formula (IIb), supra, which is then reacted with the corresponding phenol $R^2OH$ or thiophenol $R^2SH$.

The conversion from the alcohol to the halide or sulfonate ester of formula (IIb) is carried out by means well known in the art. For example, the alcohol may be halogenated using a halogenating agent such as thionyl chloride or thionyl bromide, either neat, or in an inert organic solvent such as dichloromethane or chloroform, at a temperature between about 0° and 80° C., preferably between about 20° and 80° C. The halogenation reaction may be carried out in the presence of a molar equivalent of a base (e.g., pyridine) if desired. Alternative halogenation procedures include, for example, the use of triphenylphosphine with either carbon tetrachloride, carbon tetrabromide, or N-chloro- or N-bromosuccinimide. When utilizing thionyl chloride or thionyl bromide without the use of added base, the hydrochloride or hydrobromide salt of the corresponding halo compound is produced. This salt may be neutralized (e.g., with potassium carbonate) prior to its use in the alkylation step, or the salt may be used directly if excess phenol or thiophenol salt or base is utilized.

Sulfonate esters may be prepared by the standard procedure of treating the alcohol with at least a stoichiometric amount to approximately a 100% excess (preferably 10%–20% excess) of, for example, methanesulfonyl chloride or p-toluenesulfonyl chloride, in the presence of a base, for example, pyridine or triethylamine. This reaction is carried out at a temperature from about −20° to +50° C., preferably between about 0° and 20° C.

The halide or sulfonate ester prepared as described above, is then treated with a metal salt, preferably an alkali metal salt such as the sodium or potassium salt, of the corresponding phenol or thiophenol, in the presence of an inert organic solvent such as acetone, dimethylsulfoxide, dimethylformamide, methanol, and the like, at a temperature of about 20° to about 100° C. If desired, the metal salt of the phenol or thiophenol may be preformed prior to addition of the halide.

The metal salt of the thiophenol may be prepared, for example, by reacting the thiophenol with a suitable base such as an alkali metal carbonate, hydroxide or alkoxide, e.g., potassium carbonate in the presence of a solvent such as acetone or methanol or by using an alkali metal hydride such as sodium hydride in an inert solvent. The metal salt of the phenol may be prepared by reacting the phenol with a base such as an alkali metal hydride such as sodium hydride in the presence of a solvent such as dimethylsulfoxide, dimethylformamide, tetrahydrofuran and the like. Alternatively, this transformation may be carried out under phase-transfer conditions by general methods well known to those skilled in the art, for example, by reaction of the compound of formula (IIb) with the corresponding phenol or thiophenol in a mixture of an inert organic solvent such as a chlorinated hydrocarbon (e.g., methylene chloride) and an aqueous base such as an aqueous alkali metal hydroxide (e.g., sodium hydroxide) in the presence of a quaternary phosphonium or ammonium salt such as a tetrabutylammonium salt.

Compounds of formula (I) wherein Z is S and $R^2$ is substituted or unsubstituted benzyl may be prepared by reacting the above mentioned halide or sulfonate ester of formula (IIb) with the metal salt, preferably an alkali metal salt such as the sodium or potassium salt, of a thiol $R^2SH$. This reaction is carried out in an inert organic solvent such as, for example, tetrahydrofuran, diethylether, methanol, and the like. The salt is formed with a strong base such as, for example, sodium hydride, sodium amide, sodium methoxide and the like, at a temperature between about 20° and 80° C. This transformation may also be performed using phase-transfer conditions as described above using the appropriate benzylthiol.

Compounds of formula (I) wherein $R^2$ is phenyl or substituted phenyl and Z is sulfur may also be prepared from compounds of formula (IIa) by reaction with a tri(loweralkyl)phosphine such as tri(n-butyl)phosphine and the corresponding sulfenimide as described in Tetrahedron Letters, No. 51, pp. 4475–4478 (1977).

The compounds of formula (I) may also be prepared by the reaction sequence shown below:

REACTION SEQUENCE C

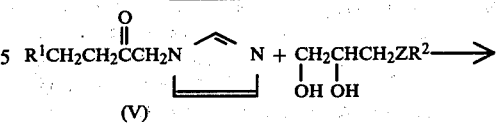

(V)

-continued
REACTION SEQUENCE C

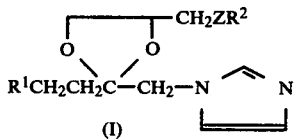

wherein $R^1$, $R^2$ and Z are as defined above.

The ketones of formula (V) are ketalized by the methods described hereinabove. The diols are well known or may be readily prepared, for example, by the general method described in J. Am. Chem. Soc., 72:3710 (1950).

Another method for preparing compounds of formula (I) is depicted in the reaction sequence shown below:

Reaction Sequence D

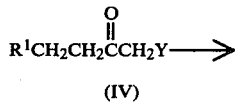

(IV)

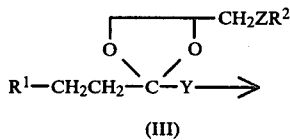

(III)

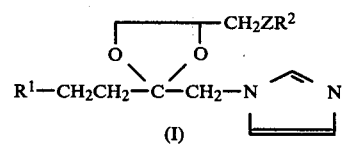

(I)

wherein $R^1$, $R^2$, Y and Z are as defined above.

The halo ketone of formula (IV) is ketalized with an ethylene glycol of the formula

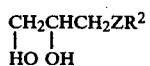

wherein $R^2$ and Z are as defined above to form compounds of formula (III) under the reaction conditions as described in part (d), Reaction Sequence B. The compounds of formula (I) are prepared by reacting the ketal intermediate of formula (III) with imidazole and/or an imidazole salt as described in part (e) in Reaction Sequence B.

The halo ketones of formula (IV) are prepared by the methods described in part (a), Reaction Sequence A.

The ethylene glycols of the above formula are prepared as described in Reaction Sequence C.

Compounds of formula (I) and the intermediates of formulas (IIa), (IIb), (III) and (VII) exist as geometric (cis and trans) isomers. (As used herein, the designations "cis" and "trans" are assigned according to the Sequence Rule as described in Org. Chem., 35:2849, 1970). The geometric isomers may be separated by various methods, for example, selective crystallization, column chromatography and high pressure liquid chromatography. When the stereochemistry is not otherwise known, it is conventionally agreed to designate the geometric isomer which is first isolated as "A" and the second as "B", without further reference to actual stereochemical configuration. Both geometric isomers as well as mixtures thereof are intended to be included within the scope of the present invention.

Many compounds of formulas (I), (IIa), (IIb), (III) and (VII) may be separated into their cis and trans isomers by chromatography. A particular useful method for separation of compounds of formula (I) and (IIb) into the respective isomers consists of chromatographing the isomeric mixture on silica gel and eluting with ethyl acetate containing 0-4%, preferably 2% of water.

A particularly useful method is the separation of the mesylate esters by the method described for compounds of formula (I) above. The individual mesylate esters of compounds of formula (IIb) may be used directly in the preparation of the individual cis and trans isomers of compounds of formula (I) by the methods described hereinabove.

Alcohols of formulas (IIa) or the acid addition salts thereof and alcohols of formula (VII) may be separated into their individual geometric isomers by esterifying the alcohol with, e.g., benzoyl chloride or 4-phenylbenzoyl chloride. The isomeric esters may be separated by, e.g., fractional crystallization or by chromatography. The individual isomeric esters are then hydrolyzed to the individual isomeric alcohol by using, e.g., an alkali metal hydroxide in aqueous methanol or dioxane.

Compounds of formula (I) do not possess a plane of symmetry about the dioxolane ring. Accordingly, the compounds of the present invention may be prepared in either optically active form, or as a racemic mixture. Unless otherwise specified, the compounds described herein are all in the racemic form. However, the scope of the subject invention herein is not be be considered limited to the racemic form, but to encompass the individual optical isomers of the subject compounds.

If desired, racemic intermediates or final products prepared herein may be resolved into their optical antipodes by conventional resolution means known per se, for example, by the separation (e.g. fractional crystallization) of the diastereomeric salts formed by reaction of, e.g., racemic compounds of formulas (I), (IIa) or (IIb) with an optically active acid, or by the separation of the diastereomeric esters formed by reaction of racemic compounds of formula (IIa), and the diastereomeric esters formed by the reaction of the racemic intermediates of formula (VII) (supra), with an optically active acid. Exemplary of such optically active acids are the optically active forms of camphor-10-sulfonic acid, α-bromo-camphor-π-sulfonic acid, camphoric acid, menthoxyacetic acid, tartaric acid, malic acid, diacetyltartaric acid, pyrrolidone-5-carboxylic acid, and the like. The separated pure diastereomeric salts or esters may then be cleaved by standard means to afford the respective optical isomers of the compounds of formula (I), (IIa) or (IIb).

PREPARATION 1

A solution of 1-chloro-4-(4-chlorophenyl)-2-butanol (125 g) in acetone (200 ml) at 0° C. was treated with 570 ml of Jones reagent (from sodium dichromate dihydrate (100 g), concentrated sulfuric acid (136 g) and water to 500 ml) and stirred overnight at room temperature. The resulting solution was diluted with water (200 ml), extracted with ether (3×300 ml) and the extracts washed with water, aqueous sodium bicarbonate, and dried (MgSO$_4$). Evaporation of the ether gave 121 g of 1-chloro-4-(4-chlorophenyl)-2-butanone. The analytical sample from hexane had m.p. 65°-67° C.

Similarly, proceeding as above, substituting the appropriate haloalcohol for 1-chloro-4-(4-chlorphenyl)-2-butanol the following compounds, for example, are prepared:

1-chloro-4-phenyl-2-butanone,
1-chloro-4-(4-bromophenyl)-2-butanone,
1-chloro-4-(4-fluorophenyl)-2-butanone,
1-chloro-4-(2,4-dichlorophenyl)-2-butanone,
1-chloro-4-(2,4,6-trichlorophenyl)-2-butanone,
1-chloro-4-(4-methylphenyl)-2-butanone,
1-chloro-4-(4-t-butylphenyl)-2-butanone,
1-chloro-4-(4-methoxyphenyl)-2-butanone, and
1-chloro-4-(4-n-butoxyphenyl)-2-butanone.

PREPARATION 2

1-Chloro-4-(4-chlorophenyl)-2-butanone (110 g) was added portionwise over half an hour to a stirred suspension of imidazole (175 g) in dimethylformamide (150 ml) at 0° C. and the mixture stirred overnight at ambient temperature. The resulting solution was poured into water (1500 ml) with seeding at the first sign of turbidity, and the precipitate filtered off and washed well with water and hexane. Chromatography of the product on silica gel (1 Kg.), eluting with 7% methanol in methylene chloride gave 100 g of 1-[4-(4-chlorophenyl)butan-2-on-1-yl]imidazole.

The hydrochloride salt from acetone/methanol had m.p. 172.5°–174° C.

Similarly, proceeding as above, substituting the appropriate haloketone for 1-chloro-4-(4-chlorophenyl)-2-butanone, there may be prepared, for example, the following compounds:

1-[4-phenylbutan-2-on-1-yl]imidazole,
1-[4-(4-bromophenyl)butan-2-on-1-yl]imidazole,
1-[4-(4-fluorophenyl)butan-2-on-1-yl]imidazole,
1-[4-(2,4-dichlorophenyl)butan-2-on-1-yl]imidazole,
1-[4-(2,4,6-trichlorophenyl)butan-2-on-1-yl]imidazole,
1-[4-(4-methylphenyl)butan-2-on-1-yl]imidazole,
1-[4-(4-t-butylphenyl)butan-2-on-1-yl]imidazole,
1-[4-(4-methoxyphenyl)butan-2-on-1-yl]imidazole, and
1-[4-(4-n-butoxyphenyl)butan-2-on-1-yl]imidazole.

PREPARATION 3

A mixture of 1-[4-(4-chlorophenyl)butan-2-on-1-yl]imidazole (50 g), p-toluenesulfonic acid monohydrate (42.07 g) and glycerol (37 g) in toluene (200 ml) was heated under reflux, with stirring, through a Dean-Stark trap for 6 hours. The two layers were allowed to separate and the hot toluene (upper layer) decanted and discarded. The lower layer was poured into 2 N sodium hydroxide (500 ml), the transfer completed by washing the flask with 1 N sodium hydroxide and methylene chloride, and the product extracted with methylene chloride (4×200 ml).

The extracts were dried (MgSO₄), evaporated and the residue recrystallized from toluene to give 61.4 g of (cis+trans)-1-[[2-(2-(4-chlorophenyl)ethyl)-4-hydroxymethyl-1,3-dioxolan-2-yl]methyl]imidazole, m.p. 96°–110° C.

Similarly, proceeding as above, substituting the appropriate imidazole ketone for 1-[4-(4-chlorophenyl)butan-2-on-1-yl]imidazole, the following compounds, for example, are prepared:

1-[[2-(2-phenylethyl)-4-hydroxymethyl-1,3-dioxolan-2-yl]methyl]imidazole,
1-[[2-(2-(4-bromophenyl)ethyl)-4-hydroxymethyl-1,3-dioxolan-2-yl]methyl]imidazole,
1-[[2-(2-(4-fluorophenyl)ethyl)-4-hydroxymethyl-1,3-dioxolan-2-yl]methyl]imidazole,
1-[[2-(2-(2,4-dichlorophenyl)ethyl)-4-hydroxymethyl-1,3-dioxolan-2-yl]methyl]imidazole,
1-[[2-(2-(2,4,6-trichlorophenyl)ethyl)-4-hydroxymethyl-1,3-dioxolan-2-yl]methyl]imidazole,
1-[[2-(2-(4-methylphenyl)ethyl)-4-hydroxymethyl-1,3-dioxolan-2-yl]methyl]imidazole,
1-[[2-(2-(4-t-butylphenyl)ethyl)-4-hydroxymethyl-1,3-dioxolan-2-yl]methyl]imidazole,
1-[[2-(2-(4-methoxyphenyl)ethyl)-4-hydroxymethyl-1,3-dioxolan-2-yl]methyl]imidazole, and
1-[[2-(2-(4-n-butoxyphenyl)ethyl)-4-hydroxymethyl-1,3-dioxolan-2-yl]methyl]imidazole.

PREPARATION 4

(A) A solution of (cis+trans)-1-[[2-(2-(4-chlorophenyl)ethyl)-4-hydroxymethyl-1,3-dioxolan-2-yl]methyl]imidazole (10.0 g) in pyridine (40 ml) at 0°–5° C. was treated over 5 minutes with stirring with 4.2 ml of benzoyl chloride. After stirring overnight, the solid mass was treated with ether (250 ml) and the resulting crude hydrochloride salt of (cis+trans)-1-[[2-(2-(4-chlorophenyl)ethyl)-4-benzoyloxymethyl-1,3-dioxolan-2-yl]methyl]imidazole was filtered off and washed well with ether. This solid was extracted twice with boiling acetone (200 ml), filtered hot, and the resulting solid recrystallized from methanol/acetone to give trans-1-[[2-(2-(4-chlorophenyl)ethyl)-4-benzoyloxymethyl-1,3-dioxolan-2-yl]methyl]imidazole hydrochloride as a snow white solid (4.38 g), m.p. 198.5°–202°. The acetone extracts from above when allowed to stand at room temperature precipitated cis-1-[[2-(2-(4-chlorophenyl)ethyl)-4-benzoyloxymethyl-1,3-dioxolan-2-yl]methyl]imidazole hydrochloride, recrystallized from acetone with m.p. 154.5°–158° C.

To obtain further material the mother liquors and mixed fraction from above were evaporated, basified by stirring with aqueous potassium carbonate and ethyl acetate and chromatographed on silica gel eluting with ethyl acetate containing 2.2% water. The first fraction consisted of pure cis-1-[[2-(2-(4-chlorophenyl)ethyl)-4-benzoyloxymethyl-1,3-dioxolan-2-yl]methyl]imidazole as an oil.

Further elution gave, after a small mixed fraction, pure trans-1-[[2-(2-(4-chlorophenyl)ethyl)-4-benzoyloxymethyl-1,3-dioxolan-2-yl]methyl]imidazole as an oil which crystallized on standing.

(B) A solution of cis-1-[[2-(2-(4-chlorophenyl)ethyl)-4-benzoyloxymethyl-1,3-dioxolan-2-yl]methyl]imidazole (2.3 g) in methanol (50 ml) was treated with sodium hydroxide (2.0 g) in water (15 ml) and the mixture stirred at room temperature until reaction was complete. The methanol was evaporated giving an oil which spontaneously crystallized on cooling of the aqueous mixture. Filtration and recrystallization from ethyl acetate gave 1.56 g of cis-1-[[2-(2-(4-chlorophenyl)ethyl)-4-hydroxymethyl-1,3-dioxolan-2-yl]methyl]imidazole, m.p. 116°–117.5° C.

Similarly, hydrolysis of trans-1-[[2-(2-(4-chlorophenyl)ethyl)-4-benzoyloxymethyl-1,3-dioxolan-2-yl]methyl]imidazole hydrochloride (3.04 g) gave 1.96 g. of trans-1-[[2-(2-(4-chlorophenyl)ethyl)-4-hydroxymethyl-1,3-dioxolan-2-yl]methyl]imidazole, m.p. 121°–122.5° C.

Alternatively, using 4-phenylbenzoyl chloride, there may be obtained (cis+trans)-1-[[2-(2-(4-chlorophenyl)ethyl)-4-(4-phenylbenzoyloxymethyl)-1,3-dioxolan-2-yl]methyl]imidazole, separable by chromatography on silica gel as above to give the respective isomers:

Cis-1-[[2-(2-(4-chlorophenyl)ethyl)-4-(4-phenylbenzoyloxymethyl)-1,3-dioxolan-2-yl]methyl]imidazole; as hydrochloride salt m.p. 180°–182.5° C., and Trans-1-[[2-(2-(4-chlorophenyl)ethyl)-4-(4-phenylbenzoyloxymethyl)-1,3-dioxolan-2-yl]methyl]imidazole; as hydrochloride salt m.p. 135.5°–140° C.

Hydrolysis of these esters in a similar manner to that described in part B for the benzoate esters is productive of the individual cis and trans isomer respectively of 1-[[2-(2-(4-chlorophenyl)ethyl)-4-hydroxymethyl-1,3-dioxolan-2-yl]methyl]imidazole.

Similarly proceeding as above, the ketal alcohols of Preparation 2 may be separated into their A and B isomers.

PREPARATION 5

(A) (Cis+trans)-1-[[2-(2-(4-chlorophenyl)ethyl)-4-hydroxymethyl-1,3-dioxolan-2-yl]methyl]imidiazole (39.7 g) in pyridine (150 ml) at 0° C. was treated dropwise with stirring with methanesulfonyl chloride (10.6 ml) and the mixture stirred overnight. The resulting solid mass was stirred with ether (500 ml) to break up the solid, filtered and washed well with ether to give (cis+trans) 1-[[2-(2-(4-chlorophenyl)ethyl)-4-methanesulfonyloxymethyl-1,3-dioxolan-2-yl]-methyl]imidazole hydrochloride. A sample recrystallized from dichloromethane/isopropanol had m.p. 107°–111° C. (coalesces).

(B) The remaining solid form part (A) was basified with aqueous potassium carbonate solution, extracted with ethyl acetate (2×400 ml) and the extracts washed, dried (MgSO$_4$) and evaporated. The resulting semicrystalline mass was chromatographed on silica gel (900 g) eluting initially with dichloromethane, followed by aqueous ethyl acetate (2.2% water) to give 25.4 g. of cis-1-[[2-(2-(4-chlorophenyl)ethyl)-4-methanesulfonyloxymethyl-1,3-dioxolan-2-yl]methyl]imidazole as a snow white solid, m.p. 93.5°–96° C.

Further elution gave, after a small mixed fraction, pure trans-1-[[2-(2-(4-chlorophenyl)ethyl)-4-methanesulfonyloxymethyl-1,3-dioxolan-2-yl]methyl]imidazole as a white solid, m.p. 93°–95° C.

(The isomers are readily distinguished by their NMR spectra, and by their behavior on silica gel thin-layer plates when eluted with ethyl acetate saturated with water).

(C) Alternatively, proceeding as in part (A) above using cis-1-[[2-(2-(4-chlorophenyl)ethyl)-4-hydroxymethyl-1,3-dioxolan-2-yl]methyl]imidazole there may be obtained cis-1-[[2-(2-(4-chlorophenyl)ethyl)-4-methanesulfonyloxymethyl-1,3-dioxolan-2-yl]methyl]imidazole recrystallized from ethyl acetate/ether with m.p. 93.5°–96° C., and using trans-1-[[2-(2-(4-chlorophenyl)ethyl)-4-hydroxymethyl-1,3-dioxolan-2-yl]methyl]imidazole gave trans-1-[[2-(2-(4-chlorophenyl)ethyl)-4-methanesulfonyloxymethyl-1,3-dioxolan-2-yl]methyl]imidazole recrystallized from ether with m.p. 93°–95° C.

PREPARATION 6

(A) 1-Bromo-4-(4-chlorophenyl)-2-butanone prepared by the method described in Preparation 1 from 1-bromo-4-(4-chlorophenyl)-2-butanol is purified by chromatography on silica gel eluting with methylene chloride. The resulting solid was recrystallized from hexane to give 1-bromo-4-(4-chlorophenyl)-2-butanone.

A mixture of 1-bromo-4-(4-chlorophenyl)-2-butanone (8.5 g), glycerol (6.38 g), and p-toluenesulfonic acid (200 mg) in toluene (150 ml) were stirred and heated under reflux using a Dean-Stark trap overnight. The resulting mixture was poured into excess aqueous potassium carbonate solution and the toluene layer separated, washed with water, dried (MgSO$_4$) and evaporated. The residue was chromatographed on silica gel eluting with 1% methanol in methylene chloride to give pure (cis+trans)-2-bromomethyl-2-[2-(4-chlorophenyl)ethyl]-4-hydroxymethyl-1,3-dioxolane as an oil.

(B) A solution of (cis+trans)-2-bromomethyl-2-[2-(4-chlorophenyl)ethyl]-4-hydroxymethyl-1,3-dioxolane (7.06 g) in pyridine (28 ml) at 0° C. was treated dropwise over 10 minutes with stirring with benzoyl chloride (3.0 ml) and stirred overnight. The resulting mixture was poured into aqueous potassium carbonate, extracted with ether (200 ml), and the extract washed with 1 N hydrochloric acid until the washings were acidic, followed by aqueous potassium carbonate solution. After drying (MgSO$_4$), removal of the ether gave (cis+trans)-2-bromoethyl-2-[2-(4-chlorophenyl)ethyl]-4-benzoyloxymethyl-1,3-dioxolane as an oil (9.8 g).

Chromatography on silica gel eluting with 20 to 30% ether in hexane gave pure cis-2-bromomethyl-2-[2-(4-chlorophenyl)ethyl]-4-benzoyloxymethyl-1,3-dioxolane as an oil. After rechromatography of the subsequent fractions eluting with 30% ether in hexane there was next obtained pure trans-2-bromomethyl-2-[2-(4-chlorophenyl)ethyl]-4-(4-benzoyloxymethyl-1,3-dioxolane as an oil.

(C) Similarly, proceeding as in part (A) above, substituting the appropriate haloketone for 1-chloro-4-(4-chlorophenyl)-2-butanone there is prepared, for example, the following compounds:

2-bromomethyl-2-(2-phenylethyl)-4-benzoyloxymethyl-1,3-dioxolane, 2-bromomethyl-2-[2-(4-bromophenyl)ethyl]-4-benzoyloxymethyl-1,3-dioxolane, 2-bromomethyl-2-[2-(4-fluorophenyl)ethyl]-4-benzoyloxymethyl-1,3-dioxolane, 2-bromomethyl-2-[2-(2,4-dichlorophenyl)ethyl]-4-benzoyloxymethyl-1,3-dioxolane, 2-bromomethyl-2-[2-(2,4,6-trichlorophenyl)ethyl]-4-benzoyloxymethyl-1,3-dioxolane, 2-bromomethyl-2-[2-(4-methylphenyl)ethyl]-4-benzoyloxymethyl-1,3-dioxolane, 2-bromomethyl-2-[2-(4-t-butylphenyl)ethyl]-4-benzoyloxymethyl-1,3-dioxolane, 2-bromomethyl-2-[2-(4-methoxyphenyl)ethyl]-4-benzoyloxymethyl-1,3-dioxolane, and 2-bromomethyl-2-[2-(4-n-butoxyphenyl)ethyl]-4-benzoyloxymethyl-1,3-dioxolane.

(D) Similarly, proceeding as in part (B) above, the compounds of part (C) may be separated into their cis and trans isomers.

PREPARATION 7

(A) A solution of cis-2-bromomethyl-2-[2-(4-chlorophenyl)ethyl]-4-benzoyloxymethyl-1,3-dioxolane (4.29 g) in methanol (50 ml) containing water (0.5 ml) was treated with potassium carbonate (500 mg) and heated under reflux overnight. After removal of the solvent, the residue was extracted with ether and the extract washed, dried (MgSO$_4$) and evaporated. Chromatography on silica eluting with 2% methanol in methylene chloride gave cis-2-bromomethyl-2-[2-(4-chlorophenyl)ethyl]-4-hydroxymethyl-1,3-dioxolane.

Similarly, proceeding as above using trans-2-bromomethyl-2-[2-(4-chlorophenyl)ethyl]-4-benzoyloxymethyl-1,3-dioxolane gives trans-2-bromomethyl-2-[2-(4-chlorophenyl)ethyl]-4-hydroxymethyl-1,3-dioxolane.

The stereochemistry of the respective isomers was determined by spectroscopic methods.

(B) Similarly, proceeding as in part (A) above the compounds of part (C), Preparation 5 are hydrolyzed to the alcohol ketal.

PREPARATION 8

(A) A mixture of (cis+trans)-2-bromomethyl-2-[2-(4-chlorophenyl)ethyl]-4-hydroxymethyl-1,3-dioxolane (1.01 g) and imidazole (0.87 g) in 15 ml of anhydrous dimethylacetamide was heated under reflux with stirring under nitrogen for 5 days. After distillation of the solvent under reduced pressure, water was added, the mixture extracted with ethyl acetate, and the extracts washed and evaporated. The residue in methanol (20 ml) was treated with excess aqueous sodium hydroxide at room temperature to hydrolyse some acetylated product, followed by removal of the methanol, addition of water and re-extraction with ethyl acetate as above. The product was chromatographed on silica gel eluting with 10% methanol in methylene chloride to give (cis+trans)-1-[[2-(2-(4-chlorophenyl)ethyl)-4-hydroxymethyl-1,3-dioxolan-2-yl]methyl]imidazole.

(B) Alternatively, proceeding as in part (A) above using cis-2-bromomethyl-2-[2-(4-chlorophenyl)ethyl]-4-hydroxymethyl-1,3-dioxolane there may be obtained cis-1-[[2-(2-(4-chlorophenyl)ethyl)-4-hydroxymethyl-1,3-dioxolan-2-yl]methyl]imidazole and using trans-2-bromomethyl-2-[2-(4-chlorophenyl)ethyl]-4-hydroxymethyl-1,3-dioxolane gave trans-1-[[2-(2-(4-chlorophenyl)ethyl)-4-hydroxymethyl-1,3-dioxolan-2-yl]methyl]imidazole.

(C) Similarly, proceeding as in part (A) above the following compounds are prepared:
1-[[2-(2-phenylethyl)-4-hydroxymethyl-1,3-dioxolan-2-yl]methyl]imidazole,
1-[[2-(2-(4-bromophenyl)ethyl)-4-hydroxymethyl-1,3-dioxolan-2-yl]methyl]imidazole,
1-[[2-(2-(4-fluorophenyl)ethyl)-4-hydroxymethyl-1,3-dioxolan-2-yl]methyl]imidazole,
1-[[2-(2-(2,4-dichlorophenyl)ethyl)-4-hydroxymethyl-1,3-dioxolan-2-yl]methyl]imidazole,
1-[[2-(2-(2,4,6-trichlorophenyl)ethyl)-4-hydroxymethyl-1,3-dioxolan-2-yl]methyl]imidazole,
1-[[2-(2-(4-methylphenyl)ethyl)-4-hydroxymethyl-1,3-dioxolan-2-yl]methyl]imidazole,
1-[[2-(2-(4-t-butylphenyl)ethyl)-4-hydroxymethyl-1,3-dioxolan-2-yl]methyl]imidazole,
1-[[2-(2-(4-methoxyphenyl)ethyl)-4-hydroxymethyl-1,3-dioxolan-2-yl]methyl]imidazole, and
1-[[2-(2-(4-n-butoxyphenyl)ethyl)-4-hydroxymethyl-1,3-dioxolan-2-yl]methyl]imidazole.

PREPARATION 9

(A) A mixture of (cis+trans)-2-bromomethyl-2-[2-(4-chlorophenyl)ethyl]-4-benzyloxymethyl-1,3-dioxolane (2.2 g), and imidazole (1.75 g) in dry dimethylacetamide (10 ml) were heated under reflux under nitrogen for five days. After distillation of the solvent under reduced pressure, water was added and the product extracted with ethyl acetate (3×75 ml). The combined extracts were washed, dried (MgSO$_4$) and evaporated to give crude (cis+trans)-1-[[2-(2-(4-chlorophenyl)ethyl)-4-benzoyloxymethyl-1,3-dioxolan-2-yl]methyl]imidazole which was hydrolysed directly as described in Preparation 6 to give (cis+trans)-1-[[2-(2-(4-chlorophenyl)ethyl)-4-hydroxymethyl-1,3-dioxolan-2-yl]methyl]imidazole.

Similarly, starting from cis-2-bromomethyl-2-[2-(4-chlorophenyl)ethyl]-4-benzoyloxymethyl-1,3-dioxolane there may be obtained cis-1-[[2-(2-(4-chlorophenyl)ethyl)-4-benzoyloxymethyl-1,3-dioxolan-2-yl]methyl]imidazole and starting from trans-2-bromomethyl-2-[2-(4-chlorophenyl)ethyl]-4-benzoyloxymethyl-1,3-dioxolane there may be obtained trans-1-[[2-(2-(4-chlorophenyl)ethyl)-4-benzoyloxymethyl-1,3-dioxolan-2-yl]methyl]imidazole, which were hydrolyzed as described in Preparation 6 to give cis-1-[[2-(2-(4-chlorophenyl)ethyl)-4-hydroxymethyl-1,3-dioxolan-2-yl]methyl]imidazole and trans-1-[[2-(2-(4-chlorophenyl)ethyl)-4-hydroxymethyl-1,3-dioxolan-2-yl]methyl]imidazole.

(B) Similarly, proceeding as in part (A) of this preparation and substituting the appropriate ketal ester for 2-bromomethyl-2-[2-(4-chlorophenyl)ethyl]-4-benzyloxymethyl-1,3-dioxolane, either the cis-trans mixture or the individual isomers thereof, the following compounds are prepared:
1-[[2-(2-phenylethyl)-4-hydroxymethyl-1,3-dioxolan-2-yl]methyl]imidazole,
1-[[2-(2-(4-bromophenyl)ethyl)-4-hydroxymethyl-1,3-dioxolan-2-yl]methyl]imidazole,
1-[[2-(2-(4-fluorophenyl)ethyl)-4-hydroxymethyl-1,3-dioxolan-2-yl]methyl]imidazole,
1-[[2-(2-(2,4-dichlorophenyl)ethyl)-4-hydroxymethyl-1,3-dioxolan-2-yl]methyl]imidazole,
1-[[2-(2-(2,4,6-trichlorophenyl)ethyl)-4-hydroxymethyl-1,3-dioxolan-2-yl]methyl]imidazole,
1-[[2-(2-(4-methylphenyl)ethyl)-4-hydroxymethyl-1,3-dioxolan-2-yl]methyl]imidazole,
1-[[2-(2-(4-t-butylphenyl)ethyl)-4-hydroxymethyl-1,3-dioxolan-2-yl]methyl]imidazole,
1-[[2-(2-(4-methoxyphenyl)ethyl)-4-hydroxymethyl-1,3-dioxolan-2-yl]methyl]imidazole, and
1-[[2-(2-(4-n-butoxyphenyl)ethyl)-4-hydroxymethyl-1,3-dioxolan-2-yl]methyl]imidazole.

The following representative examples are given to further enable one to prepare specific representative compounds of this invention, but are not intended to limit the scope of the claims appended hereto. The compounds may be further characterized by their salts. Unless otherwise specified the compounds are the cis-trans geometric isomer mixture.

EXAMPLE 1

(A) 2-Chlorophenol (310 mg) in dry dimethyl sulfoxide (20 ml) was treated with sodium hydride (105 mg of 50% dispersion in mineral oil) with stirring at 85° C., followed, when evolution of hydrogen was complete, by cis-1-[[2-(2-(4-chlorophenyl)ethyl)-4-(methanesulfonyloxymethyl)-1,3-dioxolan-2-yl]methyl]imidazole (800 mg). After stirring overnight at 85° C., the mixture was poured into water (150 ml), extracted with ether (2×50 ml) and the extracts washed, dried (MgSO$_4$) and evaporated. After chromatography on a short column of silica gel eluting with 30% acetone/methylene chloride, the pure product was dissolved in ether and treated with 70% nitric acid (d=1.42) dropwise until precipitation was complete. Filtration of the solid and recrystallization from ethyl acetate/acetone gave 705 mg of cis-1-[[2-(2-(4-chlorophenyl)ethyl)-4-(2-chlorophenoxymethyl)-1,3-dioxolan-2-yl]methyl]imidazole nitrate, m.p. 150°–152° C.

Similarly, proceeding as above, substituting (cis+trans)-1-[[2-(2-(4-chlorophenyl)ethyl)-4-(methanesulfonyloxymethyl)-1,3-dioxolan-2-yl]methyl]imidazole or trans-1-[[2-(2-(4-chlorophenyl)ethyl)-4-(methanesulfonyloxymethyl)-1,3-dioxolan-2-yl]methyl]imidazole for cis-1-[[2-(2-(4-chlorophenyl)ethyl)-4-(methanesulfonyloxymethyl)-1,3-dioxolan-2-yl]methyl]imidazole there is prepared (cis+trans)-1-[[2-(2-(4-chlorophenyl)ethyl)-4-(2-chlorophenoxymethyl)-1,3-dioxolan-2-yl]methyl]imidazole or trans-1-[[2-(2-(4-chlorophenyl)ethyl)-4-(2-chlorophenoxymethyl)-1,3-dioxolan-2-yl]methyl]imidazole.

(B) Similarly, proceeding as in part (A) of this example, substituting the appropriate phenols for 2-chlorophenol the following compounds are prepared:

1-[[2-(2-(4-chlorophenyl)ethyl)-4-phenoxymethyl-1,3-dioxolan-2-yl]methyl]imidazole, 1-[[2-(2-(4-chlorophenyl)ethyl)-4-(3-chlorophenoxymethyl)-1,3-dioxolan-2-yl]methyl]imidazole, 1-[[2-(2-(4-chlorophenyl)ethyl)-4-(4-chlorophenoxymethyl)-1,3-dioxolan-2-yl]methyl]imidazole, cis isomer, nitrate salt, m.p. 133°–135° C., 1-[[2-(2-(4-chlorophenyl)ethyl)-4-(4-bromophenoxymethyl)-1,3-dioxolan-2-yl]methyl]imidazole, 1-[[2-(2-(4-chlorophenyl)ethyl)-4-(4-fluorophenoxymethyl)-1,3-dioxolan-2-yl]methyl]imidazole, 1-[[2-(2-(4-chlorophenyl)ethyl)-4-(2,4-dichlorophenoxymethyl)-1,3-dioxolan-2-yl]methyl]imidazole, cis isomer, m.p. 100°–102° C., 1-[[2-(2-4-chlorophenyl)ethyl)-4-(2,5-dichlorophenoxymethyl)-1,3-dioxolan-2-yl]methyl]imidazole, 1-[[2-(2-(4-chlorophenyl)ethyl)-4-(2,6-dichlorophenoxymethyl)-1,3-dioxolan-2-yl]methyl]imidazole, cis isomer, hydrochloride salt, m.p. 156°–159° C., 1-[[2-(2-(4-chlorophenyl)ethyl)-4-(2,4,6-trichlorophenoxymethyl)-1,3-dioxolan-2-yl]methyl]imidazole, cis isomer, hydrochloride salt, m.p. 202°–205° C., 1-[[2-(2-(4-chlorophenyl)ethyl)-4-(2-methylphenoxymethyl)-1,3-dioxolan-2-yl]methyl]imidazole, 1-[[2-(2-(4-chlorophenyl)ethyl)-4-(3-methylphenoxymethyl)-1,3-dioxolan-2-yl]methyl]imidazole, 1-[[2-(2-(4-chlorophenyl)ethyl)-4-(4-methylphenoxymethyl)-1,3-dioxolan-2-yl]methyl]imidazole, 1-[[2-(2-(4-chlorophenyl)ethyl)-4-(2,4-dimethylphenoxymethyl)-1,3-dioxolan-2-yl]methyl]imidazole, 1-[[2-(2-(4-chlorophenyl)ethyl)-4-(2,5-dimethylphenoxymethyl)-1,3-dioxolan-2-yl]methyl]imidazole, 1-[[2-(2-(4-chlorophenyl)ethyl)-4-(2,6-dimethylphenoxymethyl)-1,3-dioxolan-2-yl]methyl]imidazole, cis isomer, nitrate salt, m.p. 92°–97° C., 1-[[2-(2-(4-chlorophenyl)ethyl)-4-(2,4,6-trimethylphenoxymethyl)-1,3-dioxolan-2-yl]methyl]imidazole, cis isomer, hydrochloride salt, m.p. 153°–155° C., 1-[[2-(2-(4-chlorophenyl)ethyl)-4-(pentamethylphenoxymethyl)-1,3-dioxolan-2-yl]methyl]imidazole, 1-[[2-(2-(4-chlorophenyl)ethyl)-4-(4-t-butylphenoxymethyl)-1,3-dioxolan-2-yl]methyl]imidazole, 1-[[2-(2-(4-chlorophenyl)ethyl)-4-(4-phenylphenoxymethyl)-1,3-dioxolan-2-yl]methyl]imidazole, cis isomer, nitrate salt, m.p. 154.5°–156° C.; trans isomer, nitrate salt, m.p. 147°–149° C., 1-[[2-(2-(4-chlorophenyl)ethyl)-4-(4-(4-chlorophenyl)phenoxymethyl)-1,3-dioxolan-2-yl]methyl]imidazole, 1-[[2-(2-(4-chlorophenyl)ethyl)-4-(4-(4-methylphenyl)phenoxymethyl)-1,3-dioxolan-2-yl]methyl]imidazole, 1-[[2-(2-(4-chlorophenyl)ethyl)-4-(4-(4-methoxyphenyl)phenoxymethyl)-1,3-dioxolan-2-yl]methyl]imidazole, 1-[[2-(2-(4-chlorophenyl)ethyl)-4-(4-(4-trifluoromethylphenyl)phenoxymethyl)-1,3-dioxolan-2-yl]methyl]imidazole, 1-[[2-(2-(4-chlorophenyl)ethyl)-4-(2-methoxyphenoxymethyl)-1,3-dioxolan-2-yl]methyl]imidazole, 1-[[2-(2-(4-chlorophenyl)ethyl)-4-(3-methoxyphenoxymethyl)-1,3-dioxolan-2-yl]methyl]imidazole, 1-[[2-(2-(4-chlorophenyl)ethyl)-4-(4-methoxyphenoxymethyl)-1,3-dioxolan-2-yl]methyl]imidazole, 1-[[2-(2-(4-chlorophenyl)ethyl)-4-(4-n-butoxyphenoxymethyl)-1,3-doxolan-2-yl]methyl]imidazole, and 1-[[2-(2-(4-chlorophenyl)ethyl)-4-(4-trifluoromethylphenoxymethyl)-1,3-dioxolan-2-yl]methyl]imidazole.

(C) Similarly, proceeding as in part (A) of this example, substituting the appropriate phenols for 2-chlorophenol and substituting 1-[[2-(2-phenylethyl)-4-(methanesulfonoxymethyl)-1,3-dioxolan-2-yl]methyl]imidazole for 1-[[2-(2-(4-chlorophenyl)ethyl)-4-(methanesulfonyloxymethyl)-1,3-dioxolan-2-yl]methyl]imidazole the following compounds are prepared:

1-[[2-(2-phenylethyl)-4-(4-chlorophenoxymethyl)-1,3-dioxolan-2-yl]methyl]imidazole, 1-[[2-(2-phenylethyl)-4-(4-methylphenoxymethyl)-1,3-dioxolan-2-yl]methyl]imidazole, and 1-[[2-(2-phenylethyl)-4-(4-methoxyphenoxymethyl)-1,3-dioxolan-2-yl]methyl]imidazole.

(D) Similarly, proceeding as in part (A) of this example, substituting the appropriate phenols for 2-chlorophenol and substituting 1-[[2-(2-(4-bromophenyl)ethyl)-4-(methanesulfonyloxymethyl)-1,3-dioxolan-2-yl]methyl]imidazole for 1-[[2-(2-(4-chlorophenyl)ethyl)-4-(methanesulfonyloxymethyl)-1,3-dioxolan-2-yl]methyl]imidazole the following compounds are prepared:

1-[[2-(2-(4-bromophenyl)ethyl)-4-(4-chlorophenoxymethyl)-1,3-dioxolan-2-yl]methyl]imidazole, 1-[[2-(2-(4-bromophenyl)ethyl)-4-(4-methylphenoxymethyl)-1,3-dioxolan-2-yl]methyl]imidazole, and 1-[[2-(2-(4-bromophenyl)ethyl)-4-(4-methoxyphenoxymethyl)-1,3-dioxolan-2-yl]methyl]imidazole.

(E) Similarly, proceeding as in part (A) of this example, substituting 1-[[2-(2-(4-fluorophenyl)ethyl)-4-(methanesulfonyloxymethyl)-1,3-dioxolan-2-yl]methyl]imidazole for 1-[[2-(2-(4-chlorophenyl)ethyl)-4-(methanesulfonyloxymethyl)-1,3-dioxolan-2-yl]methyl]imidazole there is obtained 1-[[2-(2-(4-fluorophenyl)ethyl)-4-(2-chlorophenoxymethyl)-1,3-dioxolan-2-yl]methyl]imidazole. By substituting the appropriate phenols for 2-chlorophenol and substituting 1-[[2-(2-(4-fluorophenyl)ethyl)-4-(methanesulfonyloxymethyl)-1,3-dioxolan-2-yl]methyl]imidazole for 1-[[2-(2-(4-chlorophenyl)ethyl)-4-(methanesulfonyloxymethyl)-1,3-dioxolan-2-yl]methyl]imidazole the following compounds are prepared:

1-[[2-(2-(4-fluorophenyl)ethyl)-4-phenoxymethyl-1,3-dioxolan-2-yl]methyl]imidazole,
1-[[2-(2-(4-fluorophenyl)ethyl)-4-(3-chlorophenoxymethyl)-1,3-dioxolan-2-yl]methyl]imidazole,
1-[[2-(2-(4-fluorophenyl)ethyl)-4-(4-chlorophenoxymethyl)-1,3-dioxolan-2-yl]methyl]imidazole,
1-[[2-(2-(4-fluorophenyl)ethyl)-4-(4-bromophenoxymethyl)-1,3-dioxolan-2-yl]methyl]imidazole,
1-[[2-(2-(4-fluorophenyl)ethyl)-4-(4-fluorophenoxymethyl)-1,3-dioxolan-2-yl]methyl]imidazole,
1-[[2-(2-(4-fluorophenyl)ethyl)-4-(2,4-dichlorophenoxymethyl)-1,3-dioxolan-2-yl]methyl]imidazole,
1-[[2-(2-(4-fluorophenyl)ethyl)-4-(2,5-dichlorophenoxymethyl)-1,3-dioxolan-2-yl]methyl]imidazole,
1-[[2-(2-(4-fluorophenyl)ethyl)-4-(2,6-dichlorophenoxymethyl)-1,3-dioxolan-2-yl]methyl]imidazole,
1-[[2-(2-(4-fluorophenyl)ethyl)-4-(2,4,6-trichlorophenoxymethyl)-1,3-dioxolan-2-yl]methyl]imidazole,
1-[[2-(2-(4-fluorophenyl)ethyl)-4-(2-methylphenoxymethyl)-1,3-dioxolan-2-yl]methyl]imidazole,
1-[[2-(2-(4-fluorophenyl)ethyl)-4-(3-methylphenoxymethyl)-1,3-dioxolan-2-yl]methyl]imidazole,
1-[[2-(2-(4-fluorophenyl)ethyl)-4-(4-methylphenoxymethyl)-1,3-dioxolan-2-yl]methyl]imidazole,
1-[[2-(2-(4-fluorophenyl)ethyl)-4-(2,5-dimethylphenoxymethyl)-1,3-dioxolan-2-yl]methyl]imidazole,
1-[[2-(2-(4-fluorophenyl)ethyl)-4-(2,6-dimethylphenoxymethyl)-1,3-dioxolan-2-yl]methyl]imidazole,
1-[[2-(2-(4-fluorophenyl)ethyl)-4-(2,4,6-trimethylphenoxymethyl)-1,3-dioxolan-2-yl]methyl]imidazole,
1-[[2-(2-(4-fluorophenyl)ethyl)-4-(4-t-butylphenoxymethyl)-1,3-dioxolan-2-yl]methyl]imidazole,
1-[[2-(2-(4-fluorophenyl)ethyl)-4-(4-(4-chlorophenyl)phenoxymethyl)-1,3-dioxolan-2-yl]methyl]imidazole,
1-[[2-(2-(4-fluorophenyl)ethyl)-4-(4-(4-methylphenyl)phenoxymethyl)-1,3-dioxolan-2-yl]methyl]imidazole,
1-[[2-(2-(4-fluorophenyl)ethyl)-4-(4-(4-methoxyphenyl)phenoxymethyl)-1,3-dioxolan-2-yl]methyl]imidazole,
1-[[2-(2-(4-fluorophenyl)ethyl)-4-(4-(4-trifluoromethylphenyl)phenoxymethyl)-1,3-dioxolan-2-yl]methyl]imidazole,
1-[[2-(2-(4-fluorophenyl)ethyl)-4-(4-phenylphenoxymethyl)-1,3-dioxolan-2-yl]methyl]imidazole,
1-[[2-(2-(4-fluorophenyl)ethyl)-4-(2-methoxyphenoxymethyl)-1,3-dioxolan-2-yl]methyl]imidazole,
1-[[2-(2-(4-fluorophenyl)ethyl)-4-(2,4-dimethylphenoxymethyl)-1,3-dioxolan-2-yl]methyl]imidazole,
1-[[2-(2-(4-fluorophenyl)ethyl)-4-(4-methoxyphenoxymethyl)-1,3-dioxolan-2-yl]methyl]imidazole,
1-[[2-(2-(4-fluorophenyl)ethyl)-4-(4-n-butoxyphenoxymethyl)-1,3-dioxolan-2-yl]methyl]imidazole, and
1-[[2-(2-(4-fluorophenyl)ethyl)-4-(4-(trifluoromethyl)phenoxymethyl)-1,3-dioxolan-2-yl]methyl]imidazole.

(F) Similarly, proceeding as in part (A) of this example, substituting the appropriate phenols for 2-chlorophenol and substituting 1-[[2-(2-(2,4-dichlorophenyl)ethyl)-4-(methanesulfonyloxymethyl)-1,3-dioxolan-2-yl]methyl]-imidazole for 1-[[2-(2-(4-chlorophenyl)ethyl)-4-(methanesulfonyloxymethyl)-1,3-dioxolan-2-yl]methyl]imidazole the following compounds are prepared:

1-[[2-(2-(2,4-dichlorophenyl)ethyl)-4-(4-chlorophenoxymethyl)-1,3-dioxolan-2-yl]methyl]imidazole,
1-[[2-(2-(2,4-dichlorophenyl)ethyl)-4-(4-methylphenoxymethyl)-1,3-dioxolan-2-yl]methyl]imidazole, and
1-[[2-(2-(2,4-dichlorophenyl)ethyl)-4-(4-methoxyphenoxymethyl)-1,3-dioxolan-2-yl]methyl]imidazole.

(G) Similarly, proceeding as in part (A) of this example, substituting the appropriate phenols for 2-chlorophenol and substituting 1-[[2-(2-(2,4,6-trichlorophenyl)ethyl)-4-(methanesulfonyloxymethyl)-1,3-dioxolan-2-yl]methyl]imidazole for 1-[[2-(2-(4-chlorophenyl)ethyl)-4-(methanesulfonyloxymethyl)-1,3-dioxolan-2-yl]methyl]imidazole the following compounds are prepared:

1-[[2-(2-(2,4,6-trichlorophenyl)ethyl)-4-(4-chlorophenoxymethyl)-1,3-dioxolan-2-yl]methyl]imidazole,
1-[[2-(2-(2,4,6-trichlorophenyl)ethyl)-4-(4-methylphenoxymethyl)-1,3-dioxolan-2-yl]methyl]imidazole, and
1-[[2-(2-(2,4,6-trichlorophenyl)ethyl)-4-(4-methoxyphenoxymethyl)-1,3-dioxolan-2-yl]methyl]imidazole.

(H) Similarly, proceeding as in part (A) of this example, substituting 1-[[2-(2-(4-methylphenyl)ethyl)-4-(methanesulfonyloxymethyl)-1,3-dioxolan-2-yl]methyl]imidazole for 1-[[2-(2-(4-chlorophenyl)ethyl)-4-(methanesulfonyloxymethyl)-1,3-dioxolan-2-yl]methyl]imidazole there is obtained 1-[[2-(2-(4-methylphenyl)ethyl)-4-(2-chlorophenoxymethyl)-1,3-dioxolan-2-yl]methyl]imidazole. By substituting the appropriate phenols for 2-chlorophenol and substituting 1-[[2-(2-(4-methylphenyl)ethyl)-4-(methanesulfonyloxymethyl)-1,3-dioxolan-2-yl]methyl]imidazole for 1-[[2-(2-(4-chlorophenyl)ethyl)-4-(methanesulfonyloxymethyl)-1,3-dioxolan-2-yl]methyl]imidazole the following compounds are prepared:

1-[[2-(2-(4-methylphenyl)ethyl)-4-phenoxymethyl-1,3-dioxolan-2-yl]methyl]imidazole,
1-[[2-(2-(4-methylphenyl)ethyl)-4-(3-chlorophenoxymethyl)-1,3-dioxolan-2-yl]methyl]imidazole,
1-[[2-(2-(4-methylphenyl)ethyl)-4-(4-chlorophenoxymethyl)-1,3-dioxolan-2-yl]methyl]imidazole,
1-[[2-(2-(4-methylphenyl)ethyl)-4-(4-bromophenoxymethyl)-1,3-dioxolan-2-yl]methyl]imidazole,
1-[[2-(2-(4-methylphenyl)ethyl)-4-(4-fluorophenoxymethyl)-1,3-dioxolan-2-yl]methyl]imidazole,
1-[[2-(2-(4-methylphenyl)ethyl)-4-(2,4-dichlorophenoxymethyl)-1,3-dioxolan-2-yl]methyl]imidazole,
1-[[2-(2-(4-methylphenyl)ethyl)-4-(2,5-dichlorophenoxymethyl)-1,3-dioxolan-2-yl]methyl]imidazole,
1-[[2-(2-(4-methylphenyl)ethyl)-4-(2,6-dichlorophenoxymethyl)-1,3-dioxolan-2-yl]methyl]imidazole, 1-[[2-(2-(4-methylphenyl)ethyl)-4-(2,4,6-trichlorophenoxymethyl)-1,3-dioxolan-2-yl]methyl]imidazole,
1-[[2-(2-(4-methylphenyl)ethyl)-4-(2-methylphenoxymethyl)-1,3-dioxolan-2-yl]methyl]imidazole,
1-[[2-(2-(4-methylphenyl)ethyl)-4-(3-methylphenoxymethyl)-1,3-dioxolan-2-yl]methyl]imidazole,
1-[[2-(2-(4-methylphenyl)ethyl)-4-(4-methylphenoxymethyl)-1,3-dioxolan-2-yl]methyl]imidazole,
1-[[2-(2-(4-methylphenyl)ethyl)-4-(2,4-dimethylphenoxymethyl)-1,3-dioxolan-2-yl]methyl]imidazole,
1-[[2-(2-(4-methylphenyl)ethyl)-4-(2,5-dimethylphenoxymethyl)-1,3-dioxolan-2-yl]methyl]imidazole,
1-[[2-(2-(4-methylphenyl)ethyl)-4-(2,6-dimethylphenoxymethyl)-1,3-dioxolan-2-yl]methyl]imidazole,
1-[[2-(2-(4-methylphenyl)ethyl)-4-(2,4,6-trimethylphenoxymethyl)-1,3-dioxolan-2-yl]methyl]imidazole,
1-[[2-(2-(4-methylphenyl)ethyl)-4-(4-t-butylphenoxymethyl)-1,3-dioxolan-2-yl]methyl]imidazole,
1-[[2-(2-(4-methylphenyl)ethyl)-4-(4-phenylphenoxymethyl)-1,3-dioxolan-2-yl]methyl]imidazole,
1-[[2-(2-(4-methylphenyl)ethyl)-4-(4-(4-chlorophenyl)phenoxymethyl)-1,3-dioxolan-2-yl]methyl]imidazole,
1-[[2-(2-(4-methylphenyl)ethyl)-4-(4-(4-methylphenyl)phenoxymethyl)-1,3-dioxolan-2-yl]methyl]imidazole,
1-[[2-(2-(4-methylphenyl)ethyl)-4-(4-(4-methoxyphenyl)phenoxymethyl)-1,3-dioxolan-2-yl]methyl]imidazole,
1-[[2-(2-(4-methylphenyl)ethyl)-4-(4-(4-trifluoromethylphenyl)phenoxymethyl)-1,3-dioxolan-2-yl]methyl]imidazole,
1-[[2-(2-(4-methylphenyl)ethyl)-4-(2-methoxyphenoxymethyl)-1,3-dioxolan-2-yl]methyl]imidazole,
1-[[2-(2-(4-methylphenyl)ethyl)-4-(3-methoxyphenoxymethyl)-1,3-dioxolan-2-yl]methyl]imidazole,
1-[[2-(2-(4-methylphenyl)ethyl-4-(4-methoxyphenoxymethyl)-1,3-dioxolan-2-yl]methyl]imidazole,
1-[[2-(2-(4-methylphenyl)ethyl-4-(4-n-butoxyphenoxymethyl)-1,3-dioxolan-2-yl]methyl]imidazole, and
1-[[2-(2-(4-methylphenyl)ethyl)-4-(4-trifluoromethylphenoxymethyl)-1,3-dioxolan-2-yl]methyl]imidazole.

(I) Similarly, proceeding as in part (A) of this example, substituting the appropriate phenols for 2-chlorophenol and substituting 1-[[2-(2-(4-t-butylphenyl)ethyl)-4-(methanesulfonyloxymethyl)-1,3-dioxolan-2-yl]methyl]imidazole for 1-[[2-(2-(4-chlorophenyl)ethyl)-4-methanesulfonyloxymethyl)-1,3-dioxolan-2-yl]methyl]imidazole the following compounds are prepared:
1-[[2-(2-(4-t-butylphenyl)ethyl)-4-(4-chlorophenoxymethyl)-1,3-dioxolan-2-yl]methyl]imidazole,
1-[[2-(2-(4-t-butylphenyl)ethyl)-4-(4-methylphenoxymethyl)-1,3-dioxolan-2-yl]methyl]imidazole, and
1-[[2-(2-(4-t-butylphenyl)ethyl)-4-(4-methoxyphenoxymethyl)-1,3-dioxolan-2-yl]methyl]imidazole.

(J) Similarly, proceeding as in part (A) of this example, substituting 1-[[2-(2-(4-methoxyphenyl)ethyl)-4-(methanesulfonyloxymethyl)-1,3-dioxolan-2-yl]methyl]imidazole for 1-[[2-(2-(4-chlorophenyl)ethyl)-4-(methanesulfonyloxymethyl)-1,3-dioxolan-2-yl]methyl]imidazole there is obtained 1-[[2-(2-(4-methoxyphenyl)ethyl)-4-(2-chlorophenoxymethyl)-1,3-dioxolan-2-yl]methyl]imidazole. By substituting the appropriate phenols for 2-chlorophenol and substituting 1-[[2-(2-(4-methoxyphenyl)ethyl)-4-(methanesulfonyloxymethyl)-1,3-dioxolan-2-yl]methyl]imidazole for 1-[[2-(2-(4-chlorophenyl)ethyl)-4-(methanesulfonyloxymethyl)-1,3-dioxolan-2-yl]methyl]imidazole the following compounds are prepared:
1-[[2-(2-(4-methoxyphenyl)ethyl)-4-phenoxymethyl-1,3-dioxolan-2-yl]methyl]imidazole,
1-[[2-(2-(4-methoxyphenyl)ethyl)-4-(3-chlorophenoxymethyl)-1,3-dioxolan-2-yl]methyl]imidazole,
1-[[2-(2-(4-methoxyphenyl)ethyl)-4-(4-chlorophenoxymethyl)-1,3-dioxolan-2-yl]methyl]imidazole,
1-[[2-(2-(4-methoxyphenyl)ethyl)-4-(4-bromophenoxymethyl)-1,3-dioxolan-2-yl]methyl]imidazole,
1-[[2-(2-(4-methoxyphenyl)ethyl)-4-(4-fluorophenoxymethyl)-1,3-dioxolan-2-yl]methyl]imidazole,
1-[[2-(2-(4-methoxyphenyl)ethyl)-4-(2,4-dichlorophenoxymethyl)-1,3-dioxolan-2-yl]methyl]imidazole,
1-[[2-(2-(4-methoxyphenyl)ethyl)-4-(2,5-dichlorophenoxymethyl)-1,3-dioxolan-2-yl]imidazole,
1-[[2-(2-(4-methoxyphenyl)ethyl)-4-(2,6-dichlorophenoxymethoxy)-1,3-dioxolan-2-yl]methyl]imidazole,
1-[[2-(2-(4-methoxyphenyl)ethyl)-4-(2,4,6-trichlorophenoxymethyl)-1,3-dioxolan-2-yl]methyl]imidazole,
1-[[2-(2-(4-methoxyphenyl)ethyl)-4-(2-methylphenoxymethyl)-1,3-dioxolan-2-yl]methyl]imidazole,
1-[[2-(2-(4-methoxyphenyl)ethyl)-4-(3-methylphenoxymethyl)-1,3-dioxolan-2-yl]imidazole,
1-[[2-(2-(4-methoxyphenyl)ethyl)-4-(4-methoxyphenoxymethyl)-1,3-dioxolan-2-yl]methyl]imidazole,
1-[[2-(2-(4-methoxyphenyl)ethyl)-4-(2,4-dimethylphenoxymethyl)-1,3-dioxolan-2-yl]imidazole,
1-[[2-(2-(4-methoxyphenyl)ethyl)-4-(2,5-dimethylphenoxymethyl)-1,3-dioxolan-2-yl]methyl]imidazole,
1-[[2-(2-(4-methoxyphenyl)ethyl)-4-(2,6-dimethylphenoxymethyl)-1,3-dioxolan-2-yl]methyl]imidazole,
1-[[2-(2-(4-methoxyphenyl)ethyl)-4-(2,4,6-trimethylphenoxymethyl)-1,3-dioxolan-2-yl]methyl]imidazole,
1-[[2-(2-(4-methoxyphenyl)ethyl)-4-(4-t-butylphenoxymethyl)-1,3-dioxolan-2-yl]methyl]imidazole,
1-[[2-(2-(4-methoxyphenyl)ethyl)-4-(4-phenylphenoxymethyl)-1,3-dioxolan-2-yl]methyl]imidazole,
1-[[2-(2-(4-methoxyphenyl)ethyl)-4-(4-(4-chlorophenyl)phenoxymethyl)-1,3-dioxolan-2-yl]methyl]imidazole,
1-[[2-(2-(4-methoxyphenyl)ethyl)-4-(4-(4-methylphenyl)phenoxymethyl)-1,3-dioxolan-2-yl]methyl]imidazole,
1-[[2-(2-(4-methoxyphenyl)ethyl)-4-(4-(4-methoxyphenyl)phenoxymethyl)-1,3-dioxolan-2-yl]methyl]imidazole,
1-[[2-(2-(4-methoxyphenyl)ethyl)-4-(4-(4-trifluoromethylphenyl)phenoxymethyl)-1,3-dioxolan-2-yl]methyl]imidazole,
1-[[2-(2-(4-methoxyphenyl)ethyl)-4-(2-methoxyphenoxymethyl)-1,3-dioxolan-2-yl]methyl]imidazole, 1-[[2-(2-(4-methoxyphenyl)ethyl)-4-(3-methoxy-
phenoxymethyl)-1,3-dioxolan-2-yl]imidazole,
1-[[2-(2-(4-methoxyphenyl)ethyl)-4-(4-methoxy-
phenoxymethyl-1,3-dioxolan-2-yl]methyl-
]imidazole,
1-[[2-(2-(4-methoxyphenyl)ethyl)-4-(4-n-butoxy-
phenoxymethyl)-1,3-dioxolan-2-yl]methyl-
]imidazole, and
1-[[2-(2-(4-methoxyphenyl)ethyl)-4-(4-trifluorome-
thylphenoxymethyl)-1,3-dioxolan-2-yl]imidazole.

(K) Similarly, proceeding as in part (A) of this example, substituting the appropriate phenols for 2-chlorophenol and substituting 1-[[2-(2-(4-n-butoxyphenyl)ethyl)-4-(methanesulfonyloxymethyl)-1,3-dioxolan-2-yl]methyl]imidazole for 1-[[2-(2-(4-chlorophenyl)ethyl)-4-(methanesulfonyloxymethyl)-1,3-dioxolan-2-yl]methyl]imidazole the following compounds are prepared:

1-[[2-(2-(4-n-butoxyphenyl)ethyl)-4-(4-chlorophenox-
ymethyl)-1,3-dioxolan-2-yl]methyl]imidazole,
1-[[2-(2-(4-n-butoxyphenyl)ethyl)-4-(4-methyl-
phenoxymethyl)-1,3-dioxolan-2-yl]methyl-
]imidazole, and
1-[[2-(2-(4-n-butoxyphenyl)ethyl)-4-(4-methoxy-
phenoxymethyl)-1,3-dioxolan-2-yl]methyl-
]imidazole.

EXAMPLE 2

(A) A mixture of (cis+trans)-1-[[2-(2-(4-chlorophenyl)ethyl)-4-hydroxymethyl-1,3-dioxolan-2-yl]methyl]imidazole (645 mg), α,p-dichlorotoluene (355 mg) and sodium hydride (110 mg of 50% dispersion in mineral oil) in dry dimethylformamide (15 ml) was stirred under nitrogen at room temperature for 2 hours. The mixture was poured into water, extracted with ether (2×75 ml) and the extracts washed, dried (MgSO$_4$) and evaporated to give crude (cis+trans)-1-[[2-(2-(4-chlorophenyl)ethyl)-4-(4-chlorobenzyloxymethyl)-1,3-dioxolan-2-yl]methyl]imidazole. The mixture was chromatographed on a column of silica gel made up with wet ethyl acetate, and eluted with wet ethyl acetate (2.2% water) to give as the first fraction cis-1-[[2-(2-(4-chlorophenyl)ethyl)-4-(4-chlorobenzyloxymethyl)-1,3-dioxolan-2-yl]methyl]imidazole. This was converted to the nitrate salt by treatment of an ethereal solution with concentrated nitric acid (d=1.42) dropwise until precipitation was complete. Filtration, and recrystallization from ethyl acetate/ether gave a white solid, (455 mg) m.p. 64°–67.5° C.

Further elution of the column gave, after a small mixed fraction, trans-1-[[2-(2-(4-chlorophenyl)ethyl)-4-(4-chlorobenzyloxymethyl)-1,3-dioxolan-2-yl]methyl]imidazole, converted to the nitrate salt as above and recrystallized from ethyl acetate as snow-white microcrystals (240 mg) with m.p. 111°–114° C.

Alternatively proceeding from cis-1-[[2-(2-(4-chlorophenyl)ethyl)-4-hydroxymethyl-1,3-dioxolan-2-yl]methyl]imidazole there may be obtained cis-1-[[2-(2-(4-chlorophenyl)ethyl)-4-(4-chlorobenzyloxymethyl)-1,3-dioxolan-2-yl]methyl]imidazole; and proceeding from trans-1-[[2-(2-(4-chlorophenyl)ethyl)-4-hydroxymethyl-1,3-dioxolan-2-yl]methyl]imidazole there may be obtained trans-1-[[2-(2-(4-chlorophenyl)ethyl)-4-(4-chlorobenzyloxymethyl)-1,3-dioxolan-2-yl]methyl]imidazole, respectively.

(B) Similarly, proceeding as in part (A) of this example, substituting the appropriate halotoluenes for α,p-dichlorotoluene the following compounds are prepared:

1-[[2-(2-(4-chlorophenyl)ethyl)-4-benzyloxymethyl-
1,3-dioxolan-2-yl]methyl]imidazole, cis isomer,
hydrochloride salt, m.p. 73°–80° C.; trans isomer,
hydrochloride salt, m.p. 134°–138° C.,
1-[[2-(2-(4-chlorophenyl)ethyl)-4-(2-chlorobenzylox-
ymethyl)-1,3-dioxolan-2-yl]methyl]imidazole, cis
isomer, hydrochloride salt, m.p. 69°–72° C.; hydrogen oxalate salt, m.p. 117.5°–120° C.; trans isomer,
nitrate salt, m.p. 101°–105° C.,
1-[[2-(2-(4-chlorophenyl)ethyl)-4-(3-chlorobenzylox-
ymethyl)-1,3-dioxolan-2-yl]methyl]imidazole,
1-[[2-(2-(4-chlorophenyl)ethyl)-4-(4-bromobenzylox-
ymethyl)-1,3-dioxolan-2-yl]methyl]imidazole,
1-[[2-(2-(4-chlorophenyl)ethyl)-4-(4-fluorobenzylox-
ymethyl)-1,3-dioxolan-2-yl]methyl]imidazole, cis
isomer, hydrogen oxalate salt, m.p. 114°–116° C.;
trans isomer, nitrate salt, m.p. 96°–98° C.,
1-[[2-(2-(4-chlorophenyl)ethyl)-4-(2,4-dichloroben-
zyloxymethyl)-1,3-dioxolan-2-yl]methyl]imidazole,
cis isomer, hydrogen oxalate salt, m.p. 114°–116°
C.; trans isomer, nitrate salt, 105.5°–113° C. (coalesces),
1-[[2-(2-(4-chlorophenyl)ethyl)-4-(2,5-dichloroben-
zyloxymethyl)-1,3-dioxolan-2-yl]methyl]imidazole,
1-[[2-(2-(4-chlorophenyl)ethyl)-4-(2,6-dichloroben-
zyloxymethyl)-1,3-dioxolan-2-yl]methyl]imidazole;
cis isomer, hydrochloride salt, m.p. 127°–136° C.,
1-[[2-(2-(4-chlorophenyl)ethyl)-4-(2,4,6-trichloroben-
zyloxymethyl)-1,3-dioxolan-2-yl]methyl]imidazole,
1-[[2-(2-(4-chlorophenyl)ethyl)-4-(2-methylbenzylox-
ymethyl)-1,3-dioxolan-2-yl]methyl]imidazole; cis
isomer, hydrogen oxalate salt, m.p. 114.5°–116.5°
C.,
1-[[2-(2-(4-chlorophenyl)ethyl)-4-(3-methylbenzylox-
ymethyl)-1,3-dioxolan-2-yl]methyl]imidazole,
1-[[2-(2-(4-chlorophenyl)ethyl)-4-(4-methylbenzylox-
ymethyl)-1,3-dioxolan-2-yl]methyl]imidazole,
1-[[2-(2-(4-chlorophenyl)ethyl)-4-(2,4-dimethylben-
zyloxymethyl)-1,3-dioxolan-2-yl]methyl]imidazole,
1-[[2-(2-(4-chlorophenyl)ethyl)-4-(2,5-dimethylben-
zyloxymethyl)-1,3-dioxolan-2-yl]methyl]imidazole,
1-[[2-(2-(4-chlorophenyl)ethyl)-4-(2,6-dimethylben-
zyloxymethyl)-1,3-dioxolan-2-yl]methyl]imidazole,
1-[[2-(2-(4-chlorophenyl)ethyl)-4-(2,4,6-trimethyl-
benzyloxymethyl)-1,3-dioxolan-2-yl]methyl-
]imidazole,
1-[[2-(2-(4-chlorophenyl)ethyl)-4-(4-t-butylbenzylox-
ymethyl)-1,3-dioxolan-2-yl]methyl]imidazole,
1-[[2-(2-(4-chlorophenyl)ethyl)-4-(4-phenylbenzylox-
ymethyl)-1,3-dioxolan-2-yl]methyl]imidazole,
1-[[2-(2-(4-chlorophenyl)ethyl)-4-(4-(4-chloro-
phenyl)benzyloxymethyl-1,3-dioxolan-2-yl]me-
thyl]imidazole,
1-[[2-(2-(4-chlorophenyl)ethyl)-4-(4-methylphenyl)-
benzyloxymethyl-1,3-dioxolan-2-yl]methyl-
]imidazole,
1-[[2-(2-(4-chlorophenyl)ethyl)-4-(4-(4-methoxy-
phenyl)benzyloxymethyl-1,3-dioxolan-2-yl]me-
thyl]imidazole,
1-[[2-(2-(4-chlorophenyl)ethyl)-4-(4-(4-trifluorome-
thylphenyl)benzyloxymethyl-1,3-dioxolan-2-
yl]methyl]-imidazole,
1-[[2-(2-(4-chlorophenyl)ethyl)-4-(2-methoxyben-
zyloxymethyl)-1,3-dioxolan-2-yl]methyl]imidazole,
1-[[2-(2-(4-chlorophenyl)ethyl)-4-(3-methoxyben-
zyloxymethyl)-1,3-dioxolan-2-yl]methyl]imidazole,
1-[[2-(2-(4-chlorophenyl)ethyl)-4-(4-methoxyben-
zyloxymethyl)-1,3-dioxolan-2-yl]methyl]imidazole, cis isomer, hydrogen oxalate salt, m.p. 100°–104° C. (dec); trans isomer, hydrochloride salt, m.p. 148°–150° C., 1-[[2-(2-(4-chlorophenyl)ethyl)-4-(4-n-butoxybenzyloxy methyl)-1,3-dioxolan-2-yl]methyl]imidazole, and 1-[[2-(2-(4-chlorophenyl)ethyl)-4-(4-trifluoromethylbenzyloxymethyl)-1,3-dioxolan-2-yl]methyl]imidazole.

(C) Similarly, proceeding as in part (A) of this example, substituting 1-[[2-(2-phenylethyl)-4-hydroxymethyl-1,3-dioxolan-2-yl]methyl]imidazole for 1-[[2-(2-(4-chlorophenyl)ethyl)-4-hydroxymethyl-1,3-dioxolan-2-yl]methyl]-imidazole there is obtained 1-[[2-(2-phenylethyl]-4-(4-chlorobenzyloxymethyl)-1,3-dioxolan-2-yl]methyl]imidazole. By substituting the appropriate halotoluenes for α,p-dichlorotoluene and substituting 1-[[2-(2-phenylethyl)-4-hydroxymethyl-1,3-dioxolan-2-yl]methyl]imidazole for 1-[[2-(2-(4-chlorophenyl)ethyl)-4-hydroxymethyl-1,3-dioxolan-2-yl]methyl]imidazole the following compounds are prepared:

1-[[2-(2-phenylethyl)-4-(4-methylbenzyloxymethyl)-1,3-dioxolan-2-yl]methyl]imidazole, and 1-[[2-(2-phenylethyl)-4-(4-methoxybenzyloxymethyl)-1,3-dioxolan-2-yl]methyl]imidazole.

(D) Similarly, proceeding as in part (A) of this example, substituting 1-[[2-(2-(4-bromophenyl)ethyl)-4-hydroxymethyl-1,3-dioxolan-2-yl]methyl]imidazole for 1-[[2-(2-(4-chlorophenyl)ethyl)-4-hydroxymethyl-1,3-dioxolan-2-yl]methyl]imidazole there is obtained 1-[[2-(2-(4-bromophenyl)ethyl)-4-(4-chlorobenzyloxymethyl)-1,3-dioxolan-2-yl]methyl]imidazole. By substituting the appropriate halotoluenes for α,p-dichlorotoluene and substituting 1-[[2-(2-(4-bromophenyl)ethyl)-4-hydroxymethyl-1,3-dioxolan-2-yl]methyl]imidazole for 1-[[2-(2-(4-chlorophenyl)ethyl)-4-hydroxymethyl-1,3-dioxolan-2-yl]methyl]imidazole the following compounds are prepared:

1-[[2-(2-(4-bromophenyl)ethyl)-4-(4-methylbenzyloxymethyl)-1,3-dioxolan-2-yl]methyl]imidazole, and 1-[[2-(2-(4-bromophenyl)ethyl)-4-(4-methoxybenzyloxymethyl)-1,3-dioxolan-2-yl]methyl]imidazole.

(E) Similarly, proceeding as in part (A) of this example, substituting 1-[[2-(2-(4-fluorophenyl)ethyl)-4-hydroxymethyl-1,3-dioxolan-2-yl]methyl]imidazole for 1-[[2-(2-(4-chlorophenyl)ethyl)-4-hydroxymethyl-1,3-dioxolan-2-yl]methyl]-imidazole there is obtained 1-[[2-(2-(4-fluorophenyl)ethyl)-4-(4-chlorobenzyloxymethyl)-1,3-dioxolan-2-yl]methyl]imidazole. By substituting the appropriate halotoluenes for α,p-dichlorotoluene and substituting 1-[[2-(2-(4-fluorophenyl)ethyl)-4-hydroxymethyl-1,3-dioxolan-2-yl]methyl]imidazole for 1-[[2-(2-(4-chlorophenyl)ethyl)-4-hydroxymethyl-1,3-dioxolan-2-yl]methyl]imidazole the following compounds are prepared:

1-[[2-(2-(4-fluorophenyl)ethyl)-4-benzyloxymethyl-1,3-dioxolan-2-yl]methyl]imidazole, 1-[[2-(2-(4-fluorophenyl)ethyl)-4-(2-chlorobenzyloxymethyl)-1,3-dioxolan-2-yl]methyl]imidazole, 1-[[2-(2-(4-fluorophenyl)ethyl)-4-(3-chlorobenzyloxymethyl)-1,3-dioxolan-2-yl]methyl]imidazole, 1-[[2-(2-(4-fluorophenyl)ethyl)-4-(4-bromobenzyloxymethyl)-1,3-dioxolan-2-yl]methyl]imidazole, 1-[[2-(2-(4-fluorophenyl)ethyl)-4-(4-fluorobenzyloxymethyl)-1,3-dioxolan-2-yl]methyl]imidazole, 1-[[2-(2-(4-fluorophenyl)ethyl)-4-(2,4-dichlorobenzyloxymethyl)-1,3-dioxolan-2-yl]methyl]imidazole, 1-[[2-(2-(4-fluorophenyl)ethyl)-4-(2,5-dichlorobenzyloxymethyl)-1,3-dioxolan-2-yl]methyl]imidazole, 1-[[2-(2-(4-fluorophenyl)ethyl)-4-(2,6-dichlorobenzyloxymethyl)-1,3-dioxolan-2-yl]methyl]imidazole, 1-[[2-(2-(4-fluorophenyl)ethyl)-4-(2,4,6-trichlorobenzyloxymethyl)-1,3-dioxolan-2-yl]methyl]imidazole, 1-[[2-(2-(4-fluorophenyl)ethyl)-4-(2-methylbenzyloxymethyl)-1,3-dioxolan-2-yl]methyl]imidazole, 1-[[2-(2-(4-fluorophenyl)ethyl)-4-(3-methylbenzyloxymethyl)-1,3-dioxolan-2-yl]methyl]imidazole, 1-[[2-(2-(4-fluorophenyl)ethyl)-4-(4-methylbenzyloxymethyl)-1,3-dioxolan-2-yl]methyl]imidazole, 1-[[2-(2-(4-fluorophenyl)ethyl)-4-(2,4-dimethylbenzyloxymethyl)-1,3-dioxolan-2-yl]methyl]imidazole, 1-[[2-(2-(4-fluorophenyl)ethyl)-4-(2,5-dimethylbenzyloxymethyl)-1,3-dioxolan-2-yl]methyl]imidazole, 1-[[2-(2-(4-fluorophenyl)ethyl)-4-(2,6-dimethylbenzyloxymethyl)-1,3-dioxolan-2-yl]methyl]imidazole, 1-[[2-(2-(4-fluorophenyl)ethyl)-4-(2,4,6-trimethylbenzyloxymethyl)-1,3-dioxolan-2-yl]methyl]imidazole, 1-[[2-(2-(4-fluorophenyl)ethyl)-4-(4-t-butylbenzyloxymethyl)-1,3-dioxolan-2-yl]methyl]imidazole, 1-[[2-(2-(4-fluorophenyl)ethyl)-4-(4-phenylbenzyloxymethyl)-1,3-dioxolan-2-yl]methyl]imidazole, 1-[[2-(1-(4-fluorophenyl)ethyl)-4-(4-(4-chlorophenyl)benzyloxymethyl)-1,3-dioxolan-2-yl]methyl]imidazole, 1-[[2-(1-(4-fluorophenyl)ethyl)-4-(4-(4-methylphenyl)benzyloxymethyl)-1,3-dioxolan-2-yl]methyl]imidazole, 1-[[2-(1-(4-fluorophenyl)ethyl)-4-(4-(4-methoxyphenyl)benzyloxymethyl)-1,3-dioxolan-2-yl]methyl]imidazole, 1-[[2-(1-(4-fluorophenyl)ethyl)-4-(4-(4-trifluoromethylphenyl)benzyloxymethyl)-1,3-dioxolan-2-yl]methyl]imidazole, 1-[[2-(2-(4-fluorophenyl)ethyl)-4-(2-methoxybenzyloxymethyl)-1,3-dioxolan-2-yl]methyl]imidazole, 1-[[2-(2-(4-fluorophenyl)ethyl)-4-(3-methoxybenzyloxymethyl)-1,3-dioxolan-2-yl]methyl]imidazole, 1-[[2-(2-(4-fluorophenyl)ethyl)-4-(4-methoxybenzyloxymethyl)-1,3-dioxolan-2-yl]methyl]imidazole, 1-[[2-(2-(4-fluorophenyl)ethyl)-4-(4-n-butoxybenzyloxymethyl)-1,3-dioxolan-2-yl]methyl]imidazole, and 1-[[2-(2-(4-fluorophenyl)ethyl)-4-(4-trifluoromethylbenzyloxymethyl)-1,3-dioxolan-2-yl]methyl]imidazole.

(F) Similarly, proceeding as in part (A) of this example, substituting 1-[[2-(2-(2,4-dichlorophenyl)ethyl)-4-hydroxymethyl-1,3-dioxolan-2-yl]methyl]imidazole for 1-[[2-(2-(4-chlorophenyl)ethyl)-4-hydroxymethyl-1,3-dioxolan-2-yl]methyl]imidazole there is obtained 1-[[2-(2-(2,4-dichlorophenyl)ethyl)-4-(4-chlorobenzyloxymethyl)-1,3-dioxolan-2-yl]methyl]imidazole. By substituting the appropriate halotoluenes for α,p-dichlorotoluene and substituting 1-[[2-(2-(2,4-dichlorophenyl)ethyl)-4-hydroxymethyl-1,3-dioxolan-2-yl]methyl]imidazole for 1-[[2-(2-(4-chlorophenyl)ethyl)-4-hydroxymethyl-1,3-dioxolan-2-yl]methyl]imidazole the following compounds are prepared:

1-[[2-(2-(2,4-dichlorophenyl)ethyl)-4-(4-methylbenzyloxymethyl)-1,3-dioxolan-2-yl]methyl]imidazole, and 1-[[2-(2-(2,4-dichlorophenyl)ethyl)-4-(4-methoxybenzoxymethyl)-1,3-dioxolan-2-yl]methyl]imidazole.

(G) Similarly, proceeding as in part (A) of this example, substituting 1-[[2-(2-(2,4,6-trichlorophenyl)ethyl)-4- hydroxymethyl-1,3-dioxolan-2-yl]methyl]imidazole for 1-[[2-(2-(4-chlorophenyl)ethyl)-4-hydroxymethyl-1,3-dioxolan-2-yl]methyl]imidazole there is obtained 1-[[2-(2-(2,4,6-trichlorophenyl)ethyl)-4-(4-chlorobenzyloxymethyl)-1,3-dioxolan-2-yl]methyl]imidazole. By substituting the appropriate halotoluenes for α,p-dichlorotoluene and substituting 1-[[2-(2-(2,4,6-trichlorophenyl)ethyl)-4-hydroxymethyl-1,3-dioxolan-2-yl]methyl]imidazole for 1-[[2-(2-(4-chlorophenyl)ethyl)-4-hydroxymethyl-1,3-dioxolan-2-yl]methyl]imidazole the following compounds are prepared:

1-[[2-(2-(2,4,6-trichlorophenyl)ethyl)-4-(4-methylbenzyloxymethyl)-1,3-dioxolan-2-yl]methyl]imidazole, and 1-[[2-(2-(2,4,6-trichlorophenyl)ethyl)-4-(4-methoxybenzyloxymethyl)-1,3-dioxolan-2-yl]methyl]imidazole.

(H) Similarly, proceeding as in part (A) of this example, substituting 1-[[2-(2-(4-methylphenyl)ethyl)-4-hydroxymethyl-1,3-dioxolan-2-yl]methyl]imidazole for 1-[[2-(2-(4-chlorophenyl)ethyl)-4-hydroxymethyl-1,3-dioxolan-2-yl]methyl]-imidazole there is obtained 1-[[2-(2-(4-methylphenyl)ethyl)-4-(4-chlorobenzyloxymethyl)-1,3-dioxolan-2-yl]methyl]imidazole. By substituting the appropriate halotoluenes for α,p-dichlorotoluene and substituting 1-[[2-(2-(4-methylphenyl)ethyl)-4-hydroxymethyl-1,3-dioxolan-2-yl]methyl]imidazole for 1-[[2-(2-(4-chlorophenyl)ethyl)-4-hydroxymethyl-1,3-dioxolan-2-yl]methyl]imidazole the following compounds are prepared:

1-[[2-(2-(4-methylphenyl)ethyl)-4-benzyloxymethyl-1,3-dioxolan-2-yl]methyl]imidazole, 1-[[2-(2-(4-methylphenyl)ethyl)-4-(2-chlorobenzyloxymethyl)-1,3-dioxolan-2-yl]methyl]imidazole, 1-[[2-(2-(4-methylphenyl)ethyl)-4-(3-chlorobenzyloxymethyl)-1,3-dioxolan-2-yl]methyl]imidazole, 1-[[2-(2-(4-methylphenyl)ethyl)-4-(4-bromobenzyloxy)methyl)-1,3-dioxolan-2-yl]methyl]imidazole, 1-[[2-(2-(4-methylphenyl)ethyl)-4-(4-fluorobenzyloxymethyl)-1,3-dioxolan-2-yl]methyl]imidazole, 1-[[2-(2-(4-methylphenyl)ethyl)-4-(2,4-dichlorobenzyloxymethyl)-1,3-dioxolan-2-yl]methyl]imidazole, 1-[[2-(2-(4-methylphenyl)ethyl)-4-(2,5-dichlorobenzyloxymethyl)-1,3-dioxolan-2-yl]methyl]imidazole, 1-[[2-(2-(4-methylphenyl)ethyl)-4-(2,6-dichlorobenzyloxymethyl)-1,3-dioxolan-2-yl]methyl]imidazole, 1-[[2-(2-(4-methylphenyl)ethyl)-4-(2,4,6-trichlorobenzyloxymethyl)-1,3-dioxolan-2-yl]methyl]imidazole, 1-[[2-(2-(4-methylphenyl)ethyl)-4-(2-methylbenzyloxymethyl)-1,3-dioxolan-2-yl]methyl]imidazole, 1-[[2-(2-(4-methylphenyl)ethyl)-4-(3-methylbenzyloxymethyl)-1,3-dioxolan-2-yl]methyl]imidazole, 1-[[2-(2-(4-methylphenyl)ethyl)-4-(4-methylbenzyloxymethyl)-1,3-dioxolan-2-yl]methyl]imidazole, 1-[[2-(2-(4-methylphenyl)ethyl)-4-(2,4-dimethylbenzyloxymethyl)-1,3-dioxolan-2-yl]methyl]imidazole, 1-[[2-(2-(4-methylphenyl)ethyl)-4-(2,5-dimethylbenzyloxymethyl)-1,3-dioxolan-2-yl]methyl]imidazole, 1-[[2-(2-(4-methylphenyl)ethyl)-4-(2,6-dimethylbenzyloxymethyl)-1,3-dioxolan-2-yl]methyl]imidazole, 1-[[2-(2-(4-methylphenyl)ethyl)-4-(2,4,6-trimethylbenzyloxymethyl)-1,3-dioxolan-2-yl]methyl]imidazole, 1-[[2-(2-(4-methylphenyl)ethyl)-4-(4-t-butylbenzyloxymethyl)-1,3-dioxolan-2-yl]methyl]imidazole, 1-[[2-(2-(4-methylphenyl)ethyl)-4-(4-phenylbenzyloxymethyl)-1,3-dioxolan-2-yl]methyl]imidazole, 1-[[2-(2-(4-methylphenyl)ethyl)-4-(4-(4-chlorophenylbenzyloxymethyl)-1,3-dioxolan-2-yl]methyl]imidazole, 1-[[2-(2-(4-methylphenyl)ethyl)-4-(4-(4-methylphenylbenzyloxymethyl)-1,3-dioxolan-2-yl]methyl]imidazole, 1-[[2-(2-(4-methylphenyl)ethyl)-4-(4-(4-methoxyphenylbenzyloxymethyl)-1,3-dioxolan-2-yl]methyl]imidazole, 1-[[2-(2-(4-methylphenyl)ethyl)-4-(4-(4-trifluoromethylphenylbenzyloxymethyl)-1,3-dioxolan-2-yl]methyl]imidazole, 1-[[2-(2-(4-methylphenyl)ethyl)-4-(2-methoxybenzyloxymethyl)-1,3-dioxolan-2-yl]methyl]imidazole, 1-[[2-(2-(4-methylphenyl)ethyl)-4-(3-methoxybenzyloxymethyl)-1,3-dioxolan-2-yl]methyl]imidazole, 1-[[2-(2-(4-methylphenyl)ethyl)-4-(4-methoxybenzyloxymethyl)-1,3-dioxolan-2-yl]methyl]imidazole, 1-[[2-(2-(4-methylphenyl)ethyl)-4-(4-n-butoxybenzyloxymethyl)-1,3-dioxolan-2-yl]methyl]imidazole, and 1-[[2-(2-(4-methylphenyl)ethyl)-4-(4-trifluoromethylbenzyloxymethyl)-1,3-dioxolan-2-yl]methyl]imidazole.

(I) Similarly, proceeding as in part (A) of this example, substituting 1-[[2-(2-(4-t-butylphenyl)ethyl)-4-hydroxymethyl-1,3-dioxolan-2-yl]methyl]-imidazole for 1-[[2-(2-(4-chlorophenyl)ethyl)-4-hydroxymethyl-1,3-dioxolan-2-yl]methyl]imidazole there is obtained 1-[[2-(2-(4-t-butylphenyl)ethyl)-4-(4-chlorobenzyloxymethyl)-1,3-dioxolan-2-yl]methyl]imidazole. By substituting the appropriate halotoluenes for α,p-dichlorotoluene and substituting 1-[[2-(2-(4-t-butylphenyl)ethyl)-4-hydroxymethyl-1,3-dioxolan-2-yl]methyl]imidazole for 1-[[2-(2-(4-chlorophenyl)ethyl)-4-hydroxymethyl-1,3-dioxolan-2-yl]methyl]imidazole the following compounds are prepared:

1-[[2-(2-(4-t-butylphenyl)ethyl)-4-(4-methylbenzyloxymethyl)-1,3-dioxolan-2-yl]methyl]imidazole, and 1-[[2-(2-(4-t-butylphenyl)ethyl)-4-(4-methoxybenzyloxymethyl)-1,3-dioxolan-2-yl]methyl]imidazole.

(J) Similarly, proceeding as in part (A) of this example, substituting 1-[[2-(2-(4-methoxyphenyl)ethyl)-4-hydroxymethyl-1,3-dioxolan-2-yl]methyl]imidazole for 1-[[2-(2-(4-chlorophenyl)ethyl)-4-hydroxymethyl-1,3-dioxolan-2-yl]methyl]-imidazole there is obtained 1-[[2-(2-(4-methoxyphenyl)ethyl)-4-(4-chlorobenzyloxymethyl)-1,3-dioxolan-2-yl]methyl]imidazole. By substituting the appropriate halotoluenes for α,p-dichlorotoluene and substituting 1-[[2-(2-(4-methoxyphenyl)ethyl)-4-hydroxymethyl-1,3-dioxolan-2-yl]methyl]imidazole for 1-[[2-(2-(4-chlorophenyl)ethyl)-4-hydroxymethyl-1,3-dioxolan-2-yl]methyl]imidazole the following compounds are prepared:

1-[[2-(2-(4-methoxyphenyl)ethyl)-4-benzyloxymethyl-1,3-dioxolan-2-yl]methyl]imidazole, 1-[[2-(2-(4-methoxyphenyl)ethyl)-4-(2-chlorobenzyloxymethyl)-1,3-dioxolan-2-yl]methyl]imidazole, 1-[[2-(2-(4-methoxyphenyl)ethyl)-4-(3-chlorobenzyloxymethyl)-1,3-dioxolan-2-yl]methyl]imidazole, 1-[[2-(2-(4-methoxyphenyl)ethyl)-4-(4-bromobenzyloxymethyl)-1,3-dioxolan-2-yl]methyl]imidazole, 1-[[2-(2-(4-methoxyphenyl)ethyl)-4-(4-fluorobenzyloxymethyl)-1,3-dioxolan-2-yl]methyl]imidazole, 1-[[2-(2-(4-methoxyphenyl)ethyl)-4-(2,4-dichlorobenzyloxymethyl)-1,3-dioxolan-2-yl]methyl]imidazole, 1-[[2-(1-(4-methoxyphenyl)ethyl)-4-(2,5-dichlorobenzyloxymethyl)-1,3-dioxolan-2-yl]methyl]imidazole, 1-[[2-(2-(4-methoxyphenyl)ethyl)-4-(2,6-dichlorobenzyloxymethyl)-1,3-dioxolan-2-yl]methyl]imidazole,
1-[[2-(2-(4-methoxyphenyl)ethyl)-4-(2,4,6-trichlorobenzyloxymethyl)-1,3-dioxolan-2-yl]methyl]imidazole,
1-[[2-(2-(4-methoxyphenyl)ethyl)-4-(2-methylbenzyloxymethyl)-1,3-dioxolan-2-yl]methyl]imidazole,
1-[[2-(1-(4-methoxyphenyl)ethyl)-4-(3-methylbenzyloxymethyl)-1,3-dioxolan-2-yl]methyl]imidazole,
1-[[2-(2-(4-methoxyphenyl)ethyl)-4-(4-methylbenzyloxymethyl)-1,3-dioxolan-2-yl]methyl]imidazole,
1-[[2-(1-(4-methoxyphenyl)ethyl)-4-(2,4-dimethylbenzyloxymethyl)-1,3-dioxolan-2-yl]methyl]imidazole,
1-[[2-(2-(4-methoxyphenyl)ethyl)-4-(2,5-dimethylbenzyloxymethyl)-1,3-dioxolan-2-yl]methyl]imidazole,
1-[[2-(2-(4-methoxyphenyl)ethyl)-4-(2,6-dimethylbenzyloxymethyl)-1,3-dioxolan-2-yl]methyl]imidazole,
1-[[2-(2-(4-methoxyphenyl)ethyl)-4-(2,4,6-trimethylbenzyloxymethyl)-1,3-dioxolan-2-yl]methyl]imidazole,
1-[[2-(2-(4-methoxyphenyl)ethyl)-4-(4-t-butylbenzyloxymethyl)-1,3-dioxolan-2-yl]methyl]imidazole,
1-[[2-(2-(4-methoxyphenyl)ethyl)-4-(4-phenylbenzyloxymethyl)-1,3-dioxolan-2-yl]methyl]imidazole,
1-[[2-(2-(4-methoxyphenyl)ethyl)-4-(4-(4-chlorophenyl)benzyloxymethyl)-1,3-dioxolan-2-yl]methyl]imidazole,
1-[[2-(2-(4-methoxyphenyl)ethyl)-4-(4-(4-methylphenyl)benzyloxymethyl)-1,3-dioxolan-2-yl]methyl]imidazole,
1-[[2-(2-(4-methoxyphenyl)ethyl)-4-(4-(4-methoxyphenyl)benzyloxymethyl)-1,3-dioxolan-2-yl]methyl]imidazole,
1-[[2-(2-(4-methoxyphenyl)ethyl)-4-(4-(4-trifluoromethylphenyl)benzyloxymethyl)-1,3-dioxolan-2-yl]methyl]imidazole,
1-[[2-(2-(4-methoxyphenyl)ethyl)-4-(2-methoxybenzyloxymethyl)-1,3-dioxolan-2-yl]methyl]imidazole,
1-[[2-(1-(4-methoxyphenyl)ethyl)-4-(3-methoxybenzyloxymethyl)-1,3-dioxolan-2-yl]methyl]imidazole,
1-[[2-(2-(4-methoxyphenyl)ethyl)-4-(4-methoxybenzyloxymethyl)-1,3-dioxolan-2-yl]methyl]imidazole,
1-[[2-(2-(4-methoxyphenyl)ethyl)-4-(4-n-butoxybenzyloxymethyl)-1,3-dioxolan-2-yl]methyl]imidazole, and
1-[[2-(1-(4-methoxyphenyl)ethyl)-4-(4-trifluoromethylbenzyloxymethyl)-1,3-dioxolan-2-yl]methyl]imidazole.

(K) Similarly, proceeding as in part (A) of this example, substituting 1-[[2-(2-(4-n-butoxyphenyl)ethyl)-4-hydroxymethyl-1,3-dioxolan-2-yl]methyl]imidazole for 1-[[2-(2-(4-chlorophenyl)ethyl)-4-hydroxymethyl-1,3-dioxolan-2-yl]methyl]imidazole there is obtained 1-[[2-(2-(4-n-butoxyphenyl)ethyl)-4-(4-chlorobenzyloxymethyl)-1,3-dioxolan-2-yl]methyl]imidazole. By substituting the appropriate halotoluenes for α,p-dichlorotoluene and substituting 1-[[2-(2-(4-n-butoxyphenyl)ethyl)-4-hydroxymethyl-1,3-dioxolan-2-yl]methyl]imidazole for 1-[[2-(2-(4-chlorophenyl)ethyl)-4-hydroxymethyl-1,3-dioxolan-2-yl]methyl]imidazole the following compounds are prepared:

1-[[2-(2-(4-n-butoxyphenyl)ethyl)-4-(4-methylbenzyloxymethyl)-1,3-dioxolan-2-yl]methyl]imidazole, and
1-[[2-(2-(4-n-butoxyphenyl)ethyl)-4-(4-methoxybenzyloxymethyl)-1,3-dioxolan-2-yl]methyl]imidazole.

EXAMPLE 3

(A) A mixture of cis-1-[[2-(2-(4-chlorophenyl)ethyl)-4-(methanesulfonyloxymethyl)-1,3-dioxolan-2-yl]methyl]imidazole (600 mg), 4-chlorothiophenol (250 mg) and anhydrous potassium carbonate (230 mg) in acetone was stirred and heated under reflux overnight. After removal of the solvent and addition of water (30 ml), the mixture was extracted with ether (2×50 ml), and the extracts washed and dried (MgSO$_4$).

The nitrate salt was precipitated by dropwise addition of concentrated nitric acid (d=1.42), and recrystallized from ethyl acetate/ether to give cis-1-[[2-(2-(4-chlorophenyl)ethyl)-4-(4-chlorophenylthiomethyl)-1,3-dioxolan-2-yl]methyl]imidazole nitrate, m.p. 130°–132° C.

Similarly, using trans-1-[[2-(2-(4-chlorophenyl)ethyl)-4-(methanesulfonyloxymethyl)-1,3-dioxolan-2-yl]methyl]imidazole there may be prepared trans-1-[[2-(2-(4-chlorophenyl)ethyl)-4-(4-chlorophenylthiomethyl)-1,3-dioxolan-2-yl]methyl]imidazole nitrate, m.p. 110°–112.5° C. or using (cis+trans)-1-[[2-(2-(4-chlorophenyl)ethyl)-4-(methanesulfonyloxymethyl)-1,3-dioxolan-2-yl]methyl]imidazole there may be prepared (cis+trans)-1-[[2-(2-(4-chlorophenyl)ethyl)-4-(4-chlorophenylthiomethyl)-1,3-dioxolan-2-yl]methyl]imidazole, hydrogen oxalate salt, m.p. 103°–112° C. (coalesces).

(B) Similarly, proceeding as in part (A) of this example, substituting the appropriate thiophenols for 4-chlorothiophenol the following compounds are prepared:

1-[[2-(2-(4-chlorophenyl)ethyl)-4-phenylthiomethyl-1,3-dioxolan-2-yl]methyl]imidazole, hydrogen oxalate salt, m.p. 127°–134° C. (coalesces); cis isomer, hydrochloride salt, m.p. 146.5°–148.5° C.,
1-[[2-(2-(4-chlorophenyl)ethyl)-4-(2-chlorophenylthiomethyl)-1,3-dioxolan-2-yl]methyl]imidazole, hydrogen oxalate salt, m.p. 130°–136° C. (coalesces); cis isomer, nitrate salt, m.p. 140°–142° C.,
1-[[2-(2-(4-chlorophenyl)ethyl)-4-(3-chlorophenylthiomethyl)-1,3-dioxolan-2-yl]methyl]imidazole, cis isomer, hydrochloride salt, m.p. 125°–127° C.,
1-[[2-(2-(4-chlorophenyl)ethyl)-4-(4-bromophenylthiomethyl)-1,3-dioxolan-2-yl]methyl]imidazole,
1-[[2-(2-(4-chlorophenyl)ethyl)-4-(4-fluorophenylthiomethyl)-1,3-dioxolan-2-yl]methyl]imidazole,
1-[[2-(2-(4-chlorophenyl)ethyl)-4-(2,4-dichlorophenylthiomethyl)-1,3-dioxolan-2-yl]methyl]imidazole,
1-[[2-(2-(4-chlorophenyl)ethyl)4-(2,5-dichlorophenylthiomethyl)-1,3-dioxolan-2-yl]methyl]imidazole,
1-[[2-(2-(4-chlorophenyl)ethyl)-4-(2,6-dichlorophenylthiomethyl)-1,3-dioxolan-2-yl]methyl]imidazole, cis isomer, nitrate salt, m.p. 166°–168° C. (foaming),
1-[[2-(2-(4-chlorophenyl)ethyl)-4-(2,4,6-trichlorophenylthiomethyl)-1,3-dioxolan-2-yl]methyl]imidazole,
1-[[2-(2-(4-chlorophenyl)ethyl)-4-(pentachlorophenylthiomethyl)-1,3-dioxolan-2-yl]methyl]imidazole,
1-[[2-(2-(4-chlorophenyl)ethyl)-4-(2-methylphenylthiomethyl)-1,3-dioxolan-2-yl]methyl]imidazole, cis isomer, hydrochloride salt, m.p. 77°–79° C. (coalesces), 1-[[2-(2-(4-chlorophenyl)ethyl)4-(3-methylphenylthiomethyl)-1,3-dioxolan-2-yl]methyl]imidazole, 1-[[2-(2-(4-chlorophenyl)ethyl)-4-(4-methylphenylthiomethyl)-1,3-dioxolan-2-yl]methyl]imidazole, cis isomer, hydrochloride salt, m.p. 168.5°–171° C., 1-[[2-(2-(4-chlorophenyl)ethyl)4-(2,4-dimethylphenylthiomethyl)-1,3-dioxolan-2-yl]methyl]imidazole, 1-[[2-(2-(4-chlorophenyl)ethyl)-4-(2,5-dimethylphenylthiomethyl)-1,3-dioxolan-2-yl]methyl]imidazole, cis isomer, hydrochloride salt, m.p. 84°–87° C. (coalesces), 1-[[2-(2-(4-chlorophenyl)ethyl)-4-(2,6-dimethylphenylthiomethyl)-1,3-dioxolan-2-yl]methyl]imidazole, cis isomer, nitrate salt, m.p. 149°–150° C., 1-[[2-(2-(4-chlorophenyl)ethyl)-4-(2,4,6-trimethylphenylthiomethyl)-1,3-dioxolan-2-yl]methyl]imidazole, cis isomer, hydrochloride salt, m.p. 174.5°–178° C., 1-[[2-(2-(4-chlorophenyl)ethyl)-4-(4-t-butylphenylthiomethyl)-1,3-dioxolan-2-yl]methyl]imidazole, 1-[[2-(2-(4-chlorophenyl)ethyl)-4-(4-phenylphenylthiomethyl)-1,3-dioxolan-2-yl]methyl]imidazole, 1-[[2-(2-(4-chlorophenyl)ethyl)-4-(4-(4-chlorophenyl)phenylthiomethyl)-1,3-dioxolan-2-yl]methyl]imidazole, 1-[[2-(2-(4-chlorophenyl)ethyl)-4-(4-(4-methylphenyl)phenylthiomethyl)-1,3-dioxolan-2-yl]methyl]-imidazole, 1-[[2-(2-(4-chlorophenyl)ethyl)-4-(4-(4-methoxyphenyl)phenylthiomethyl)-1,3-dioxolan-2-yl]methyl]imidazole, 1-[[2-(2-(4-chlorophenyl)ethyl)-4-(4-(4-trifluoromethylphenyl)phenylthiomethyl)-1,3-dioxolan-2-yl]methyl]-imidazole, 1-[[2-(2-(4-chlorophenyl)ethyl)-4-(2-methoxyphenylthiomethyl)-1,3-dioxolan-2-yl]methyl]imidazole, cis isomer, hydrochloride salt, m.p. 161°–162.5° C., 1-[[2-(2-(4-chlorophenyl)ethyl)-4-(3-methoxyphenylthiomethyl)-1,3-dioxolan-2-yl]methyl]imidazole, 1-[[2-(2-(4-chlorophenyl)ethyl)-4-(4-methoxyphenylthiomethyl)-1,3-dioxolan-2-yl]methyl]imidazole, 1-[[2-(2-(4-chlorophenyl)ethyl)-4-(4-n-butoxyphenylthiomethyl)-1,3-dioxolan-2-yl]methyl]imidazole, 1-[[2-(2-(4-chlorophenyl)ethyl)-4-(4-trifluoromethylphenylthiomethyl)-1,3-dioxolan-2-yl]methyl]imidazole, 1-[[2-(2-(4-chlorophenyl)ethyl)-4-(2-chloro-4-methoxyphenylthiomethyl)-1,3-dioxolan-2-yl]methyl]imidazole, and 1-[[2-(2-(4-chlorophenyl)ethyl)-4-(2-chloro-6-methylphenylthiomethyl)-1,3-dioxolan-2-yl]methyl]imidazole.

(C) Similarly, proceeding as in part (A) of this example, substituting 1-[[2-(2-phenylethyl)-4-(methanesulfonyloxymethyl)-1,3-dioxolan-2-yl]methyl]imidazole for 1-[[2-(2-(4-chlorophenyl)ethyl)-4-(methanesulfonyloxymethyl)-1,3-dioxolan-2-yl]methyl]imidazole there is obtained 1-[[2-(2-phenylethyl)-4-(4-chlorophenylthiomethyl)-1,3-dioxolan-2-yl]methyl]imidazole. By substituting the appropriate thiophenols for 4-chlorothiophenol and substituting 1-[[2-(2-phenylethyl)-4-(methanesulfonyloxymethyl)-1,3-dioxolan-2-yl]methyl]imidazole for 1-[[2-(2-(4-chlorophenyl)ethyl)-4-(methanesulfonyloxymethyl)-1,3-dioxolan-2-yl]methyl]imidazole the following compounds are prepared:

1-[[2-(2-phenylethyl)-4-(4-methylphenylthiomethyl)-1,3-dioxolan-2-yl]methyl]imidazole, and 1-[[2-(2-phenylethyl)-4-(4-methoxyphenylthiomethyl)-1,3-dioxolan-2-yl]methyl]imidazole.

(D) Similarly, proceeding as in part (A) of this example, substituting 1-[[2-(2-(4-bromophenyl)ethyl)-4-(methanesulfonyloxymethyl)-1,3-dioxolan-2-yl]methyl]imidazole for 1-[[2-(2-(4-chlorophenyl)ethyl)-4-(methanesulfonyloxymethyl)-1,3-dioxolan-2-yl]methyl]imidazole there is obtained 1-[[2-(2-(4-bromophenyl)ethyl)-4-(4-chlorophenyl-thiomethyl)-1,3-dioxolan-2-yl]methyl]imidazole. By substituting the appropriate thiophenols for 4-chlorothiophenol and substituting 1-[[2-(2-(4-bromophenyl)ethyl)-4-(methanesulfonyloxymethyl)-1,3-dioxolan-2-yl]methyl]imidazole for 1-[[2-(2-(4-chlorophenyl)ethyl)-4-(methanesulfonyloxymethyl)-1,3-dioxolan-2-yl]methyl]imidazole the following compounds are prepared:

1-[[2-(2-(4-bromophenyl)ethyl)-4-(4-methylphenylthiomethyl)-1,3-dioxolan-2-yl]methyl]imidazole, and 1-[[2-(2-(4-bromophenyl)ethyl)-4-(4-methoxyphenylthiomethyl)-1,3-dioxolan-2-yl]methyl]imidazole.

(E) Similarly, proceeding as in part (A) of this example, substituting 1-[[2-(2-(4-fluorophenyl)ethyl)-4-(methanesulfonyloxymethyl)-1,3-dioxolan-2-yl]methyl]imidazole for 1-[[2-(2-(4-chlorophenyl)ethyl)-4-(methanesulfonyloxymethyl)-1,3-dioxolan-2-yl]methyl]imidazole there is obtained 1-[[2-(2-(4-fluorophenyl)ethyl)-4-(4-chlorophenylthiomethyl)-1,3-dioxolan-2-yl]methyl]imidazole. By substituting the appropriate thiophenols for 4-chlorothiophenol and substituting 1-[[2-(2-(4-fluorophenyl)ethyl)-4-(methanesulfonyloxymethyl)-1,3-dioxolan-2-yl]methyl]imidazole for 1-[[2-(2-(4-chlorophenyl)ethyl)-4-(methanesulfonyloxymethyl)-1,3-dioxolan-2-yl]methyl]imidazole the following compounds are prepared:

1-[[2-(2-(4-fluorophenyl)ethyl)-4-phenylthiomethyl-1,3-dioxolan-2-yl]methyl]imidazole, 1-[[2-(2-(4-fluorophenyl)ethyl)-4-(2-chlorophenylthiomethyl)-1,3-dioxolan-2-yl]methyl]imidazole, 1-[[2-(2-(4-fluorophenyl)ethyl)-4-(3-chlorophenylthiomethyl)-1,3-dioxolan-2-yl]methyl]imidazole, 1[[2-(2-(4-fluorophenyl)ethyl)-4-(4-bromophenylthiomethyl)-1,3-dioxolan-2-yl]methyl]imidazole, 1-[[2-(2-(4-fluorophenyl)ethyl)-4-(4-fluorophenylthiomethyl)-1,3-dioxolan-2-yl]methyl]imidazole, 1-[[2-(2-(4-fluorophenyl)ethyl)-4-(2,4-dichlorophenylthiomethyl)-1,3-dioxolan-2-yl]methyl]imidazole, 1-[[2-(2-(4-fluorophenyl)ethyl-4-(2,5-dichlorophenylthiomethyl)-1,3-dioxolan-2-yl]methyl]imidazole, 1-[[2-(2-(4-fluorophenyl)ethyl)-4-(2,6-dichlorophenylthiomethyl)-1,3-dioxolan-2-yl]methyl]imidazole, 1-[[2-(2-(4-fluorophenyl)ethyl)-4-(2,4,6-trichlorophenylthiomethyl)-1,3-dioxolan-2-yl]methyl]imidazole, 1-[[2-(2-(4-fluorophenyl)ethyl)-4-(2-methylphenylthiomethyl)-1,3-dioxolan-2-yl]methyl]imidazole, 1-[[2-(2-(4-fluorophenyl)ethyl-4-(3-methylphenylthiomethyl)-1,3-dioxolan-2-yl]methyl]imidazole, 1-[[2-(2-(4-fluorophenyl)ethyl)-4-(4-methylphenylthiomethyl)-1,3-dioxolan-2-yl]methyl]imidazole, 1-[[2-(2-(4-fluorophenyl)ethyl-4-(2,4-dimethylphenylthiomethyl)-1,3-dioxolan-2-yl]methyl]imidazole, 1-[[2-(2-(4-fluorophenyl)ethyl)-4-(2,5-dimethyl-phenylthiomethyl)-1,3-dioxolan-2-yl]methyl]imidazole,
1-[[2-(2-(4-fluorophenyl)ethyl)-4-(2,6-dimethyl-phenylthiomethyl)-1,3-dioxolan-2-yl]methyl]imidazole,
1-[[2-(2-(4-fluorophenyl)ethyl)-4-(2,4,6-trimethyl-phenylthiomethyl)-1,3-dioxolan-2-yl]methyl]imidazole,
1-[[2-(2-(4-fluorophenyl)ethyl)-4-(4-t-butylphenylthiomethyl)-1,3-dioxolan-2-yl]methyl]imidazole,
1-[[2-(2-(4-fluorophenyl)ethyl)-4-(4-phenylphenylthiomethyl)-1,3-dioxolan-2-yl]methyl]imidazole,
1-[[2-(2-(4-fluorophenyl)ethyl)-4-(4-(4-chlorophenyl)phenylthiomethyl)-1,3-dioxolan-2-yl]methyl]imidazole,
1-[[2-(2-(4-fluorophenyl)ethyl)-4-(4-(4-methylphenyl)phenylthiomethyl)-1,3-dioxolan-2-yl]methyl]imidazole,
1-[[2-(2-(4-fluorophenyl)ethyl)-4-(4-(4-methoxyphenyl)phenylthiomethyl)-1,3-dioxolan-2-yl]methyl]imidazole,
1-[[2-(2-(4-fluorophenyl)ethyl)-4-(4-(4-trifluoromethylphenyl)phenylthiomethyl)-1,3-dioxolan-2-yl]methyl]imidazole,
1-[[2-(2-(4-fluorophenyl)ethyl)-4-(2-methoxyphenylthiomethyl)-1,3-dioxolan-2-yl]methyl]imidazole,
1-[[2-(2-(4-fluorophenyl)ethyl-4-(3-methoxyphenylthiomethyl)-1,3-dioxolan-2-yl]methyl]imidazole,
1-[[2-(2-(4-fluorophenyl)ethyl)-4-(4-methoxyphenylthiomethyl)-1,3-dioxolan-2-yl]methyl]imidazole,
1-[[2-(2-(4-fluorophenyl)ethyl)-4-(4-n-butoxyphenylthiomethyl)-1,3-dioxolan-2-yl]methyl]imidazole, and
1-[[2-(2-(4-fluorophenyl)ethyl-4-(4-trifluloromethylphenylthiomethyl)-1,3-dioxolan-2-yl]methyl]imidazole.

(F) Similarly, proceeding as in part (A) of this example, substituting 1-[[2-(2-(2,4-dichlorophenyl)ethyl)-4-(methanesulfonyloxymethyl)-1,3-dioxolan-2-yl]methyl]imidazole for 1-[[2-(2-(4-chlorophenyl)ethyl)-4-(methanesulfonyloxymethyl)-1,3-dioxolan2-yl]methyl]imidazole there is obtained 1-[[2-(2-(2,4-dichlorophenyl)ethyl)-4-(4-chlorophenylthiomethyl)-1,3-dioxolan-2-yl]methyl]imidazole. By substituting the appropriate thiophenols for 4-chlorothiophenol and substituting 1-[2-(2-(2,4-dichlorophenyl)ethyl)-4-(methanesulfonyloxymethyl)-1,3-dioxolan-2-yl]methyl]imidazole for 1-[[2-(2-(4-chloro-phenyl)ethyl)-4-(methanesulfonyloxymethyl)-1,3-dioxolan-2-yl]methyl]imidazole the following compounds are prepared:
1-[[2-(2-(2,4-dichlorophenyl)ethyl)-4-(4-methyl-phenylthiomethyl)-1,3-dioxolan-2-yl]methyl]imidazole, and
1-[[2-(2-(2,4-dichlorophenyl)ethyl)-4-(4-methoxyphenylthiomethyl)-1,3-dioxolan-2-yl]methyl]imidazole.

(G) Similarly, proceeding as in part (A) of this example, substituting 1-[[2-(2-(2,4,6-trichlorophenyl)ethyl)-4-(methanesulfonyloxymethyl)-1,3-dioxolan-2-yl]methyl]imidazole for 1-[[2-(2-(4-chlorophenyl)ethyl)-4-(methanesulfonyloxymethyl)-1,3-dioxolan-2-yl]methyl]imidazole there is obtained 1[[2-(2-(2,4,6-trichlorophenyl)ethyl)-4-(4-chlorophenylthiomethyl)-1,3-dioxolan-2-yl]methyl]imidazole. By substituting the appropriate thiophenols for 4-chlorothiophenol and substituting 1-[[2-(2-(2,4,6-trichlorophenyl)ethyl)-4-(methanesulfonyloxymethyl)-1,3-dioxolan-2-yl]methyl]imidazole for 1-[[2-(2-(4-chlorophenyl)ethyl)-4-(methanesulfonyloxymethyl)-1,3-dioxolan-2-yl]methyl]imidazole the following compounds are prepared:
1-[[2-(2-(2,4,6-trichlorophenyl)ethyl)-4-(4-methyl-phenylthiomethyl)-1,3-dioxolan-2-yl]methyl]imidazole, and
1-[[2-(2-(2,4,6-trichlorophenyl)ethyl)-4-(4-methoxyphenylthiomethyl)-1,3-dioxolan-2-yl]methyl]imidazole.

(H) Similarly, proceeding as in part (A) of this example, substituting 1-[[2-(2-(4-methylphenyl)ethyl)-4-(methanesulfonyloxymethyl)-1,3-dioxolan-2-yl]methyl]imidazole for 1-[[2-(2-(4-chlorophenyl)ethyl)-4-(methanesulfonyloxymethyl)-1,3-dioxolan-2-yl]methyl]imidazole there is obtained 1-[[2-(2-(4-methylphenyl)ethyl)-4-(4-chlorophenylthiomethyl)-1,3-dioxolan-2-yl]methyl]imidazole. By substituting the appropriate thiophenols for 4-chlorothiophenol and substituting 1-[[2-(2-(4-methylphenyl)ethyl)-4-(methanesulfonyloxymethyl)-1,3-dioxolan-2-yl]methyl]imidazole for 1-[[2-(2-(4-chlorophenyl)ethyl)-4-(methanesulfonyloxymethyl)-1,3-dioxolan-2-yl]methyl]imidazole the following compounds are prepared:
1-[[2-(2-(4-methylphenyl)ethyl)-4-phenylthiomethyl-1,3-dioxolan-2-yl]methyl]imidazole,
1-[[2-(2-(4-methylphenyl)ethyl)-4-(2-chlorophenylthiomethyl)-1,3-dioxolan-2-yl]methyl]imidazole,
1-[[2-(2-(4-methylphenyl)ethyl)-4-(3-chlorophenylthiomethyl)-1,3-dioxolan-2-yl]methyl]imidazole,
1-[[2-(2-(4-methylphenyl)ethyl)-4-(4-bromophenylthiomethyl)-1,3-dioxolan-2-yl]methyl]imidazole,
1-[[2-(2-(4-methylphenyl)ethyl)-4-(4-fluorophenylthiomethyl)-1,3-dioxolan-2-yl]methyl]imidazole,
1-[[2-(2-(4-methylphenyl)ethyl)-4-(2,4-dichloro-phenylthiomethyl)-1,3-dioxolan-2-yl]methyl]imidazole,
1-[[2-(2-(4-methylphenyl)ethyl)-4-(2,5-dichloro-phenylthiomethyl)-1,3-dioxolan-2-yl]methyl]imidazole,
1-[[2-(2-(4-methylphenyl)ethyl-4-(2,6-dichloro-phenylthiomethyl)-1,3-dioxolan-2-yl]methyl]imidazole,
1-[[2-(2-(4-methylphenyl)ethyl)-4-(2,4,6-trichloro-phenylthiomethyl)-1,3-dioxolan-2-yl]methyl]imidazole,
1-[[2-(2-(4-methylphenyl)ethyl)-4-(2-methylphenylthiomethyl)-1,3-dioxolan-2-yl]methyl]imidazole,
1-[[2-(2-(4-methylphenyl)ethyl)-4-(3-methylphenylthiomethyl)-1,3-dioxolan-2-yl]methyl]imidazole,
1-[[2-(2-(4-methylphenyl)ethyl)-4-(4-methylphenylthiomethyl)-1,3-dioxolan-2-yl]methyl]imidazole,
1-[[2-(2-(4-methylphenyl)ethyl)-4-(2,4-dimethyl-phenylthiomethyl)-1,3-dioxolan-2-yl]methyl]imidazole,
1-[[2-(2-(4-methylphenyl)ethyl)-4-(2,5-dimethyl-phenylthiomethyl)-1,3-dioxolan-2-yl]methyl]imidazole,
1-[[2-(2-(4-methylphenyl)ethyl)-4-(2,6-dimethyl-phenylthiomethyl)-1,3-dioxolan-2-yl]methyl]imidazole,
1-[[2-(2-(4-methylphenyl)ethyl)-4-(2,4,6-trimethyl-phenylthiomethyl)-1,3-dioxolan-2-yl]methyl]imidazole,
1-[[2-(2-(4-methylphenyl)ethyl)-4-(4-t-butylphenyl-thiomethyl)-1,3-dioxolan-2-yl]methyl]imidazole,
1-[[2-(2-(4-methylphenyl)ethyl)-4-(4-phenylphenyl-thio)methyl-1,3-dioxolan-2-yl]methyl]imidazole, 1-[[2-(2-(4-methylphenyl)ethyl)-4-(4-(4-chlorophenyl)phenylthiomethyl)-1,3-dioxolan-2-yl]methyl]imidazole, 1-[[2-(2-(4-methylphenyl)ethyl)-4-(4-(4-methylphenyl)phenylthiomethyl)-1,3-dioxolan-2-yl]methyl]imidazole, 1-[[2-(2-(4-methylphenyl)ethyl)-4-(4-(4-methoxyphenyl)phenylthiomethyl)-1,3-dioxolan-2-yl]methyl]imidazole, 1-[[2-(2-(4-methylphenyl)ethyl)-4-(4-(4-trifluoromethylphenyl)phenylthiomethyl)-1,3-dioxolan-2-yl]methyl]imidazole, 1-[[2-(2-(4-methylphenyl)ethyl)-4-(2-methoxyphenylthiomethyl)-1,3-dioxolan-2-yl]methyl]imidazole, 1-[[2-(2-(4-methylphenyl)ethyl)-4-(3-methoxyphenylthiomethyl)-1,3-dioxolan-2-yl]methyl]imidazole, 1-[[2-(2-(4-methylphenyl)ethyl)-4-(4-methoxyphenylthiomethyl)-1,3-dioxolan-2-yl]methyl]imidazole, 1-[[2-(2-(4-methylphenyl)ethyl)-4-(4-n-butoxyphenylthiomethyl)-1,3-dioxolan-2-yl]methyl]imidazole, and 1-[[2-(2-(4-methylphenyl)ethyl)-4-(4-trifluoromethylphenylthiomethyl)-1,3-dioxolan-2-yl]methyl]imidazole.

(I) Similarly, proceeding as in part (A) of this example, substituting 1-[[2-(2-(4-t-butylphenyl)ethyl)-4-(methanesulfonyloxymethyl)-1,3-dioxolan-2-yl]methyl]imidazole for 1-[[2-(2-(4-chlorophenyl)ethyl)-4-(methanesulfonyloxymethyl)-1,3-dioxolan-2-yl]methyl]imidazole there is obtained 1-[[2-(2-(4-t-butylphenyl)ethyl)-4-(4-chlorophenylthiomethyl)-1,3-dioxolan-2-yl]methyl]imidazole. By substituting the appropriate thiophenols for 4-chlorothiophenol and substituting 1-[[2-(2-(4-t-butylphenyl)ethyl)-4-(methanesulfonyloxymethyl)-1,3-dioxolan-2-yl]methyl]imidazole for 1-[[2-(2-(4-chlorophenyl)ethyl)-4-(methanesulfonyloxymethyl)-1,3-dioxolan-2-yl]methyl]imidazole the following compounds are prepared:

1-[[2-(2-(4-t-butylphenyl)ethyl)-4-(4-methylphenylthiomethyl)-1,3-dioxolan-2-yl]methyl]imidazole, and 1-[[2-(2-(4-t-butylphenyl)ethyl)-4-(4-methoxyphenylthiomethyl)-1,3-dioxolan-2-yl]methyl]imidazole.

(J) Similarly, proceeding as in part (A) of this example, substituting 1-[[2-(2-(4-methoxyphenyl)ethyl)-4-(methanesulfonyloxymethyl)-1,3-dioxolan-2-yl]methyl]imidazole for 1-[[2-(2-(4-chlorophenyl)ethyl)-4-(methanesulfonyloxymethyl)-1,3-dioxolan-2-yl]methyl]imidazole there is obtained 1-[[2-(2-(4-methoxyphenyl)ethyl)-4-(4-chlorophenylthiomethyl)-1,3-dioxolan-2-yl]methyl]imidazole. By substituting the appropriate thiophenols for 4-chlorothiophenol and substituting 1-[[2-(2-(4-methoxyphenyl)ethyl)-4-(methanesulfonyloxymethyl)-1,3-dioxolan-2-yl]methyl]imidazole for 1-[[2-(2-(4-chlorophenyl)ethyl)-4-(methanesulfonyloxymethyl)-1,3-dioxolan-2-yl]methyl]imidazole the following compounds are prepared:

1-[[2-(2-(4-methoxyphenyl)ethyl)-4-phenylthiomethyl-1,3-dioxolan-2-yl]methyl]imidazole, 1-[[2-(2-(4-methoxyphenyl)ethyl)-4-(2-chlorophenylthiomethyl)-1,3-dioxolan-2-yl]methyl]imidazole, 1-[[2-(2-(4-methoxyphenyl)ethyl)-4-(3-chlorophenylthiomethyl)-1,3-dioxolan-2-yl]methyl]imidazole, 1-[[2-(2-(4-methoxyphenyl)ethyl)-4-(4-bromophenylthiomethyl)-1,3-dioxolan-2-yl]methyl]imidazole, 1-[[2-(2-(4-methoxyphenyl)ethyl)-4-(4-fluorophenylthiomethyl)-1,3-dioxolan-2-yl]methyl]imidazole, 1-[[2-(2-(4-methoxyphenyl)ethyl)-4-(2,4-dichlorophenylthiomethyl)-1,3-dioxolan-2-yl]methyl]imidazole, 1-[[2-(2-(4-methoxyphenyl)ethyl)-4-(2,5-dichlorophenylthiomethyl)-1,3-dioxolan-2-yl]methyl]imidazole, 1-[[2-(2-(4-methoxyphenyl)ethyl)-4-(2,6-dichlorophenylthiomethyl)-1,3-dioxolan-2-yl]methyl]imidazole, 1-[[2-(2-(4-methoxyphenyl)ethyl)-4-(2,4,6-trichlorophenylthiomethyl)-1,3-dioxolan-2-yl]methyl]imidazole, 1-[[2-(2-(4-methoxyphenyl)ethyl)-4-(2-methylphenylthiomethyl)-1,3-dioxolan-2-yl]methyl]imidazole, 1-[[2-(2-(4-methoxyphenyl)ethyl)-4-(3-methylphenylthiomethyl)-1,3-dioxolan-2-yl]methyl]imidazole, 1-[[2-(2-(4-methoxyphenyl)ethyl)-4-(4-methylphenylthiomethyl)-1,3-dioxolan-2-yl]methyl]imidazole, 1-[[2-(2-(4-methoxyphenyl)ethyl)-4-(2,4-dimethylphenylthiomethyl)-1,3-dioxolan-2-yl]methyl]imidazole, 1-[[2-(2-(4-methoxyphenyl)ethyl)-4-(2,5-dimethylphenylthiomethyl)-1,3-dioxolan-2-yl]methyl]imidazole, 1-[[2-(2-(4-methoxyphenyl)ethyl)-4-(2,6-dimethylphenylthiomethyl)-1,3-dioxolan-2-yl]methyl]imidazole, 1-[[2-(2-(4-methoxyphenyl)ethyl)-4-(2,4,6-trimethylphenylthiomethyl)-1,3-dioxolan-2-yl]methyl]imidazole, 1-[[2-(2-(4-methoxyphenyl)ethyl)-4-(4-t-butylphenylthiomethyl)-1,3-dioxolan-2-yl]methyl]imidazole, 1-[[2-(2-(4-methoxyphenyl)ethyl)-4-(4-phenylphenylthiomethyl)-1,3-dioxolan-2-yl]methyl]imidazole, 1-[[2-(2-(4-methylphenyl)ethyl)-4-(4-(4-chlorophenyl)phenylthiomethyl)-1,3-dioxolan-2-yl]methyl]-imidazole, 1-[[2-(2-(4-methylphenyl)ethyl)-4-(4-(4-methylphenyl)phenylthiomethyl)-1,3-dioxolan-2-yl]methyl]imidazole, 1-[[2-(2-(4-methylphenyl)ethyl)-4-(4-(4-methoxyphenyl)phenylthiomethyl)-1,3-dioxolan-2-yl]methyl]imidazole, 1-[[2-(2-(4-methoxyphenyl)ethyl)-4-(4-(4-trifluoromethylphenyl)phenylthiomethyl)-1,3-dioxolan-2-yl]methyl]imidazole, 1-[[2-(2-(4-methoxyphenyl)ethyl)-4-(2-methoxyphenylthiomethyl)-1,3-dioxolan-2-yl]methyl]imidazole, 1-[[2-(2-(4-methoxyphenyl)ethyl)-4-(3-methoxyphenylthiomethyl)-1,3-dioxolan-2-yl]methyl]imidazole, 1-[[2-(2-(4-methoxyphenyl)ethyl)-4-(4-methoxyphenylthiomethyl)-1,3-dioxolan-2-yl]methyl]imidazole, 1-[[2-(2-(4-methoxyphenyl)ethyl)-4-(4-n-butoxyphenylthiomethyl)-1,3-dioxolan-2-yl]methyl]imidazole, and 1-[[2-(2-(4-methoxyphenyl)ethyl)-4-(4-trifluoromethylphenylthiomethyl)-1,3-dioxolan-2-yl]methyl]imidazole.

(K) Similarly, proceeding as in part (A) of this example, substituting 1-[[2-(2-(4-n-butoxyphenyl)ethyl)-4-(methanesulfonyloxymethyl)-1,3-dioxolan-2-yl]methyl]imidazole for 1-[[2-(2-(4-chlorophenyl)ethyl)-4-(methanesulfonyloxymethyl)-1,3-dioxolan-2-yl]methyl]imidazole there is obtained 1-[[2-(2-(4-n-butoxyphenyl)ethyl)-4-(4-chlorophenylthiomethyl)-1,3-dioxolan-2- yl]methyl]imidazole. By substituting the appropriate thiophenols for 4-chlorothiophenol and substituting 1-[[2-(2-(4-n-butoxyphenyl)ethyl)-4-(methanesulfonyloxymethyl)-1,3-dioxolan-b 2-yl]methyl]imidazole for 1-[[2-(2-(4-chlorophenyl)ethyl)-4-(methanesulfonyloxymethyl)-1,3-dioxolan-2-yl]methyl]-imidazole the following compounds are prepared:

1-[[2-(2-(4-n-butoxyphenyl)ethyl)-4-(4-methylphenylthiomethyl)-1,3-dioxolan-2-yl]methyl]imidazole, and 1-[[2-(2-(4-n-butoxyphenyl)ethyl)-4-(4-methoxyphenylthiomethyl)-1,3-dioxolan-2-yl]methyl]imidazole.

(L) Similarly, proceeding as in part (a) of this example, substituting 1-[[2-(2,4,6-trimethylphenyl)ethyl)-4-(methanesulfonyloxymethyl)-1,3-dioxolan-2-yl]methyl]imidazole for 1-[[2-(2-(4-chlorophenyl)ethyl-4-(methanesulfonyloxymethyl)-1,3-dioxolan-2-yl]methyl]imidazole there is obtained 1-[[2-(2-(2,4,6-trimethylphenyl)ethyl)-4-(4-chlorophenylthiomethyl)-1,3-dioxolan-2-yl]methyl]imidazole.

EXAMPLE 4

(A) Cis-1-[[2-(2-(4-chlorophenyl)ethyl)-4-(methanesulfonyloxymethyl)-1,3-dioxolan-2-yl]methyl]imidazole (1.05 g) was added to the preformed salt from 2-chlorobenzylthiol (800 mg) and sodium hydride (200 mg of 50% dispersion in mineral oil) in dry tetrahydrofuran (50 ml), and stirred overnight at room temperature. After evaporation of the solvent, the residue was treated with water (50 ml), extracted with ether (75 ml) and the extract washed, dried (MgSO$_4$) and treated dropwise with ethereal hydrogen chloride to precipitate the hydrochloride salt. Recrystallization from ethyl acetate gave cis-1-[[2-(2-(4-chlorophenyl)ethyl)-4-(2-chlorobenzylthiomethyl)-1,3-dioxolan-2-yl]methyl]imidazole hydrochloride (840 mg), m.p. 99.5°–101° C.

Alternatively, using (cis+trans)-1-[[2-(2-(4-chlorophenyl)ethyl)-4-(methanesulfonyloxymethyl)-1,3-dioxolan-2-yl]methyl]imidazole or trans-1-[[2-(2-(4-chlorophenyl)ethyl)-4-(methanesulfonyloxymethyl)-1,3-dioxolan-2-yl]methyl]imidazole as above there may be obtained (cis+trans)-1-[[2-(2-(4-chlorophenyl)ethyl)-4-(2-chlorobenzylthiomethyl)-1,3-dioxolan-2-yl]methyl]imidazole or trans-1-[[2-(2-(4-chlorophenyl)ethyl)-4-(2-chlorobenzylthiomethyl)-1,3-dioxolan-2-yl]methyl]imidazole.

(B) Similarly, proceeding as in part (A) of this example, substituting the appropriate benzylthiols for 2-chlorobenzylthiol the following compounds are prepared:

1-[[2-(2-(4-chlorophenyl)ethyl)-4-benzylthiomethyl-1,3-dioxolan-2-yl]methyl]imidazole, cis isomer, hydrochloride salt, m.p. 125°–126° C., 1-[[2-(2-(4-chlorophenyl)ethyl)-4-(3-chlorobenzylthiomethyl)-1,3-dioxolan-2-yl]methyl]imidazole, 1-[[2-(2-(4-chlorophenyl)ethyl)-4-(4-chlorobenzylthiomethyl)-1,3-dioxolan-2-yl]methyl]imidazole, hydrogen oxalate salt, m.p. 99°–104° C. (coalesces); cis isomer, nitrate salt, m.p. 89°–92.5° C., 1-[[2-(2-(4-chlorophenyl)ethyl)-4-(4-bromobenzylthiomethyl)-1,3-dioxolan-2-yl]methyl]imidazole, 1-[[2-(2-(4-chlorophenyl)ethyl)-4-(4-fluorobenzylthiomethyl)-1,3-dioxolan-2-yl]methyl]imidazole, 1-[[2-(2-(4-chlorophenyl)ethyl)-4-(2,4-dichlorobenzylthiomethyl)-1,3-dioxolan-2-yl]methyl]imidazole, 1-[[2-(2-(4-chlorophenyl)ethyl)-4-(2,5-dichlorobenzylthiomethyl)-1,3-dioxolan-2-yl]methyl]imidazole, 1-[[2-(2-(4-chlorophenyl)ethyl)-4-(2,6-dichlorobenzylthiomethyl)-1,3-dioxolan-2-yl]methyl]imidazole, 1-[[2-(2-(4-chlorophenyl)ethyl)-4-(2,4,6-trichlorobenzylthiomethyl)-1,3-dioxolan-2-yl]methyl]imidazole, 1-[[2-(2-(4-chlorophenyl)ethyl)-4-(2-methylbenzylthiomethyl)-1,3-dioxolan-2-yl]methyl]imidazole, 1-[[2-(2-(4-chlorophenyl)ethyl-4-(3-methylbenzylthiomethyl)-1,3-dioxolan-2-yl]methyl]imidazole, 1-[[2-(2-(4-chlorophenyl)ethyl)-4-(4-methylbenzylthiomethyl)-1,3-dioxolan-2-yl]methyl]imidazole, cis isomer, hydrochloride salt, m.p. 129°–130.5° C., 1-[[2-(2-(4-chlorophenyl)ethyl-4-(2,4-dimethylbenzylthiomethyl)-1,3-dioxolan-2-yl]methyl]imidazole, 1-[[2-(2-(4-chlorophenyl)ethyl)-4-(2,5-dimethylbenzylthiomethyl)-1,3-dioxolan-2-yl]methyl]imidazole, 1-[[2-(2-(4-chlorophenyl)ethyl)-4-(2,6-dimethylbenzylthiomethyl)-1,3-dioxolan-2-yl]methyl]imidazole, 1-[[2-(2-(4-chlorophenyl)ethyl)-4-(2,4,6-trimethylbenzylthiomethyl)-1,3-dioxolan-2-yl]methyl]imidazole, 1-[[2-(2-(4-chlorophenyl)ethyl)-4-(4-t-butylbenzylthiomethyl)-1,3-dioxolan-2-yl]methyl]imidazole, 1-[[2-(2-(4-chlorophenyl)ethyl)-4-(4-phenylbenzylthiomethyl)-1,3-dioxolan-2-yl]methyl]imidazole, 1-[[2-(2-(4-chlorophenyl)ethyl)-4-(4-(4-chlorophenyl)benzyloxymethyl)-1,3-dioxolan-2-yl]methyl]imidazole, 1-[[2-(2-(4-chlorophenyl)ethyl)-4-(4-(4-methylphenyl)benzyloxymethyl)-1,3-dioxolan-2-yl]methyl]imidazole, 1-[[2-(2-(4-chlorophenyl)ethyl)-4-(4-(4-methoxyphenyl)benzyloxymethyl)-1,3-dioxolan-2-yl]methyl]imidazole, 1-[[2-(2-(4-chlorophenyl)ethyl)-4-(4-(4-trifluoromethylphenyl)benzyloxymethyl)-1,3-dioxolan-2-yl]methyl]imidazole, 1-[[2-(2-(4-chlorophenyl)ethyl)-4-(2-methoxybenzylthiomethyl)-1,3-dioxolan-2-yl]methyl]imidazole, 1-[[2-(2-(4-chlorophenyl)ethyl-4-(3-methoxybenzylthiomethyl)-1,3-dioxolan-2-yl]methyl]imidazole, 1-[[2-(2-(4-chlorophenyl)ethyl)-4-(4-methoxybenzylthiomethyl)-1,3-dioxolan-2-yl]methyl]imidazole, cis isomer, hydrochloride salt, m.p. 115°–118° C., 1-[[2-(2-(4-chlorophenyl)ethyl)-4-(4-n-butoxybenzylthiomethyl)-1,3-dioxolan-2-yl]methyl]imidazole, and 1-[[2-(2-(4-chlorophenyl)ethyl)-4-(4-trifluoromethylbenzylthiomethyl)-1,3-dioxolan-2-yl]methyl]imidazole.

(C) Similarly, proceeding as in part (A) of this example, substituting 1-[[2-(2-phenylethyl)-4-(methanesulfonyloxymethyl)-1,3-dioxolan-2-yl]methyl]imidazole for 1-[[2-(2-(4-chlorophenyl)ethyl)-4-(methanesulfonyloxymethyl)-1,3-dioxolan-2-yl]methyl]imidazole the following compounds are prepared:

1-[[2-(2-phenylethyl)-4-(4-chlorobenzylthiomethyl)-1,3-dioxolan-2-yl]methyl]imidazole, 1-[[2-(2-phenylethyl)-4-(4-methylbenzylthiomethyl)-1,3-dioxolan-2-yl]methyl]imidazole, and 1-[[2-(2-phenylethyl)-4-(4-methoxybenzylthiomethyl)-1,3-dioxolan-2-yl]methyl]imidazole.

(D) Similarly, proceeding as in part (A) of this example, substituting the appropriate benzylthiols for 2-chlorobenzylthiol and substituting 1-[[2-(2-(4-bromophenyl)ethyl)-4-(methanesulfonyloxymethyl)-1,3-dioxolan-2-yl]methyl]imidazole for 1-[[2-(2-(4-chlorophenyl)ethyl)-4-(methanesulfonyloxymethyl)-1,3-dioxolan-2-yl]methyl]imidazole the following compounds are prepared:

1-[[2-(2-(4-bromophenyl)ethyl)-4-(4-chlorobenzylthiomethyl)-1,3-dioxolan-2-yl]methyl]imidazole,
1-[[2-(2-(4-bromophenyl)ethyl)-4-(4-methylbenzylthiomethyl)-1,3-dioxolan-2-yl]methyl]imidazole, and
1-[[2-(2-(4-bromophenyl)ethyl)-4-(4-methoxybenzylthiomethyl)-1,3-dioxolan-2-yl]methyl]imidazole.

(E) Similarly, proceeding as in part (A) of this example, substituting 1-[[2-(2-(4-fluorophenyl)ethyl)-4-(methanesulfonyloxymethyl)-1,3-dioxolan-2-yl]methyl]imidazole for 1-[[2-(2-(4-chlorophenyl)ethyl)-4-(methanesulfonyloxymethyl)-1,3-dioxolan-2-yl]methyl]imidazole there is obtained 1-[[2-(2-(4-fluorophenyl)ethyl)-4-(2-chlorobenzylthiomethyl)-1,3-dioxolan-2-yl]methyl]imidazole. By substituting the appropriate benzylthiols for 2-chlorobenzylthiol and substituting 1-[[2-(2-(4-fluorophenyl)ethyl)-4-(methanesulfonyloxymethyl)-1,3-dioxolan-2-yl]methyl]imidazole for 1-[[2-(2-(4-chlorophenyl)ethyl)-4-(methanesulfonyloxymethyl)-1,3-dioxolan-2-yl]methyl]imidazole the following compounds are prepared:

1-[[2-(2-(4-fluorophenyl)ethyl)-4-benzylthiomethyl-1,3-dioxolan-2-yl]methyl]imidazole,
1-[[2-(2-(4-fluorophenyl)ethyl)-4-(3-chlorobenzylthiomethyl)-1,3-dioxolan-2-yl]methyl]imidazole,
1-[[2-(2-(4-fluorophenyl)ethyl)-4-(4-chlorobenzylthiomethyl)-1,3-dioxolan-2-yl]methyl]imidazole,
1-[[2-(2-(4-fluorophenyl)ethyl)-4-(4-bromobenzylthiomethyl)-1,3-dioxolan-2-yl]methyl]imidazole,
1-[[2-(2-(4-fluorophenyl)ethyl)-4-(4-fluorobenzylthiomethyl)-1,3-dioxolan-2-yl]methyl]imidazole,
1-[[2-(2-(4-fluorophenyl)ethyl)-4-(2,4-dichlorobenzylthiomethyl)-1,3-dioxolan-2-yl]methyl]imidazole,
1-[[2-(2-(4-fluorophenyl)ethyl)-4-(2,5-dichlorobenzylthiomethyl)-1,3-dioxolan-2-yl]methyl]imidazole,
1-[[2-(2-(4-fluorophenyl)ethyl)-4-(2,6-dichlorobenzylthiomethyl)-1,3-dioxolan-2-yl]methyl]imidazole,
1-[[2-(2-(4-fluorophenyl)ethyl)-4-(2,4,6-trichlorobenzylthiomethyl)-1,3-dioxolan-2-yl]methyl]imidazole,
1-[[2-(2-(4-fluorophenyl)ethyl)-4-(2-methylbenzylthiomethyl)-1,3-dioxolan-2-yl]methyl]imidazole,
1-[[2-(2-(4-fluorophenyl)ethyl)-4-(3-methylbenzylthiomethyl)-1,3-dioxolan-2-yl]methyl]imidazole,
1-[[2-(2-(4-fluorophenyl)ethyl)-4-(4-methylbenzylthiomethyl)-1,3-dioxolan-2-yl]methyl]imidazole,
1-[[2-(2-(4-fluorophenyl)ethyl)-4-(2,4-dimethylbenzylthiomethyl)-1,3-dioxolan-2-yl]methyl]imidazole,
1-[[2-(2-(4-fluorophenyl)ethyl)-4-(2,5-dimethylbenzylthiomethyl)-1,3-dioxolan-2-yl]methyl]imidazole,
1-[[2-(2-(4-fluorophenyl)ethyl)-4-(2,6-dimethylbenzylthiomethyl)-1,3-dioxolan-2-yl]methyl]imidazole,
1-[[2-(2-(4-fluorophenyl)ethyl)-4-(2,4,6-trimethylbenzylthiomethyl)-1,3-dioxolan-2-yl]methyl]imidazole,
1-[[2-(2-(4-fluorophenyl)ethyl)-4-(4-t-butylbenzylthiomethyl)-1,3-dioxolan-2-yl]methyl]imidazole,
1-[[2-(2-(4-fluorophenyl)ethyl-4-(4-phenylbenzylthiomethyl)-1,3-dioxolan-2-yl]methyl]imidazole,
1-[[2-(2-(4-fluorophenyl)ethyl)-4-(4-(4-chlorophenyl)benzylthiomethyl)-1,3-dioxolan-2-yl]methyl]imidazole,
1-[[2-(2-(4-fluorophenyl)ethyl)-4-(4-(4-methylphenyl)benzylthiomethyl)-1,3-dioxolan-2-yl]methyl]imidazole,
1-[[2-(2-(4-fluorophenyl)ethyl)-4-(4-(4-methoxyphenyl)benzylthiomethyl)-1,3-dioxolan-2-yl]methyl]imidazole,
1-[[2-(2-(4-fluorophenyl)ethyl)-4-(4-(4-trifluoromethylphenyl)benzylthiomethyl)-1,3-dioxolan-2-yl]methyl]imidazole,
1-[[2-(2-(4-fluorophenyl)ethyl)-4-(2-methoxybenzylthiomethyl)-1,3-dioxolan-2-yl]methyl]imidazole,
1-[[2-(2-(4-fluorophenyl)ethyl)-4-(3-methoxybenzylthiomethyl)-1,3-dioxolan-2-yl]methyl]imidazole,
1-[[2-(2-(4-fluorophenyl)ethyl)-4-(4-methoxybenzylthiomethyl)-1,3-dioxolan-2-yl]methyl]imidazole,
1-[[2-(2-(4-fluorophenyl)ethyl)-4-(4-n-butoxybenzylthiomethyl)-1,3-dioxolan-2-yl]methyl]imidazole, and
1-[[2-(2-(4-fluorophenyl)ethyl)-4-(4-trifluoromethylbenzylthiomethyl)-1,3-dioxolan-2-yl]methyl]imidazole.

(F) Similarly, proceeding as in part (A) of this example, appropriate benzylthiols for 2-chlorobenzylthiol and substituting 1-[[2-(2-(2,4-dichlorophenyl)ethyl)-4-(methanesulfonyloxymethyl)-1,3-dioxolan-2-yl]methyl]imidazole for 1-[[2-(2-(4-chlorophenyl)ethyl)-4-(methanesulfonyloxymethyl)-1,3-dioxolan-2-yl]methyl]imidazole the following compounds are prepared:

1-[[2-(2-(2,4-dichlorophenyl)ethyl)-4-(4-chlorobenzylthiomethyl)-1,3-dioxolan-2-yl]methyl]imidazole,
1-[[2-(2-(2,4-dichlorophenyl)ethyl)-4-(4-methylbenzylthiomethyl)-1,3-dioxolan-2-yl]methyl]imidazole, and
1-[[2-(2-(2,4-dichlorophenyl)ethyl)-4-(4-methoxybenzylthiomethyl)-1,3-dioxolan-2-yl]methyl]imidazole.

(G) Similarly, proceeding as in part (A) of this example, substituting the appropriate benzylthiols for 2-chlorobenzylthiol and substituting 1-[[2-(2-(2,4,6-trichlorophenyl)ethyl)-4-(methanesulfonyloxymethyl)-1,3-dioxolan-2-yl]methyl]imidazole for 1-[[2-(2-(4-chlorophenyl)ethyl)-4-(methanesulfonyloxymethyl)-1,3-dioxolan-2-yl]methyl]imidazole the following compounds are prepared:

1-[[2-(2-(2,4,6-trichlorophenyl)ethyl)-4-(4-chlorobenzylthiomethyl)-1,3-dioxolan-2-yl]methyl]imidazole,
1-[[2-(2-(2,4,6-trichlorophenyl)ethyl)-4-(4-methylbenzylthiomethyl)-1,3-dioxolan-2-yl]methyl]imidazole, and
1-[[2-(2-(2,4,6-trichlorophenyl)ethyl)-4-(4-methoxybenzylthiomethyl)-1,3-dioxolan-2-yl]methyl]imidazole.

(H) Similarly, proceeding as in part (A) of this example, substituting 1-[[2-(2-(4-methylphenyl)ethyl)-4-(methanesulfonyloxymethyl)-1,3-dioxolan-2-yl]methyl]imidazole for 1-[[2-(2-(4-chlorophenyl)ethyl)-4-(methanesulfonyloxymethyl)-1,3-dioxolan-2-yl]methyl]imidazole there is obtained 1-[[2-(2-(4-methylphenyl)ethyl)-4-(2-chlorobenzylthiomethyl)-1,3-dioxolan-2- yl]methyl]imidazole. By substituting the appropriate benzylthiols for 2-chlorobenzylthiol and substituting 1-[[2-(2-(4-methylphenyl)ethyl)-4-(methanesulfonyloxymethyl)-1,3-dioxolan-2-yl]methyl]imidazole for 1-[[2-(2-(4-chlorophenyl)ethyl)-4-(methanesulfonyloxymethyl)-1,3-dioxolan-2-yl]methyl]imidazole the following compounds are prepared:

1-[[2-(2-(4-methylphenyl)ethyl)-4-benzylthiomethyl-1,3-dioxolan-2-yl]methyl]imidazole,
1-[[2-(2-(4-methylphenyl)ethyl)-4-(3-chlorobenzylthiomethyl)-1,3-dioxolan-2-yl]methyl]imidazole,
1-[[2-(2-(4-methylphenyl)ethyl)-4-(4-chlorobenzylthiomethyl)-1,3-dioxolan-2-yl]methyl]imidazole,
1-[[2-(2-(4-methylphenyl)ethyl)-4-(4-bromobenzylthiomethyl)-1,3-dioxolan-2-yl]methyl]imidazole,
1-[[2-(2-(4-methylphenyl)ethyl)-4-(4-fluorobenzylthiomethyl)-1,3-dioxolan-2-yl]methyl]imidazole,
1-[[2-(2-(4-methylphenyl)ethyl)-4-(2,4-dichlorobenzylthiomethyl)-1,3-dioxolan-2-yl]methyl]imidazole,
1-[[2-(2-(4-methylphenyl)ethyl)-4-(2,5-dichlorobenzylthiomethyl)-1,3-dioxolan-2-yl]methyl]imidazole,
1-[[2-(2-(4-methylphenyl)ethyl)-4-(2,6-dichlorobenzylthiomethyl)-1,3-dioxolan-2-yl]methyl]imidazole,
1-[[2-(2-(4-methylphenyl)ethyl)-4-(2,4,6-trichlorobenzylthiomethyl)-1,3-dioxolan-2-yl]methyl]imidazole,
1-[[2-(2-(4-methylphenyl)ethyl)-4-(2-methylbenzylthiomethyl)-1,3-dioxolan-2-yl]methyl]imidazole,
1-[[2-(2-(4-methylphenyl)ethyl)-4-(3-methylbenzylthiomethyl)-1,3-dioxolan-2-yl]methyl]imidazole,
1-[[2-(2-(4-methylphenyl)ethyl)-4-(4-methylbenzylthiomethyl)-1,3-dioxolan-2-yl]methyl]imidazole,
1-[[2-(2-(4-methylphenyl)ethyl)-4-(2,4-dimethylbenzylthiomethyl)-1,3-dioxolan-2-yl]methyl]imidazole,
1-[[2-(2-(4-methylphenyl)ethyl)-4-(2,5-dimethylbenzylthiomethyl)-1,3-dioxolan-2-yl]methyl]imidazole,
1-[[2-(2-(4-methylphenyl)ethyl)-4-(2,6-dimethylbenzylthiomethyl)-1,3-dioxolan-2-yl]methyl]imidazole,
1-[[2-(2-(4-methylphenyl)ethyl)-4-(2,4,6-trimethylbenzylthiomethyl)-1,3-dioxolan-2-yl]methyl]imidazole,
1-[[2-(2-(4-methylphenyl)ethyl)-4-(4-t-butylbenzylthiomethyl)-1,3-dioxolan-2-yl]methyl]imidazole,
1-[[2-(2-(4-methylphenyl)ethyl)-4-(4-phenylbenzylthiomethyl)-1,3-dioxolan-2-yl]methyl]imidazole.
1-[[2-(2-(4-methylphenyl)ethyl)-4-(4-(4-chlorophenyl)benzylthiomethyl)-1,3-dioxolan-2-yl]methyl]imidazole,
1-[[2-(2-(4-methylphenyl)ethyl)-4-(4-(4-methylphenyl)benzylthiomethyl)-1,3-dioxolan-2-yl]methyl]imidazole,
1-[[2-(2-(4-methylphenyl)ethyl)-4-(4-(4-methoxyphenyl)benzylthiomethyl)-1,3-dioxolan-2-yl]methyl]imidazole,
1-[[2-(2-(4-methylphenyl)ethyl)-4-(4-(4-trifluoromethylphenyl)benzylthiomethyl)-1,3-dioxolan-2-yl]methyl]imidazole,
1-[[2-(2-(4-methylphenyl)ethyl)-4-(2-methoxybenzylthiomethyl)-1,3-dioxolan-2-yl]methyl]imidazole,
1-[[2-(2-(4-methylphenyl)ethyl)-4-(3-methoxybenzylthiomethyl)-1,3-dioxolan-2-yl]methyl]imidazole,
1-[[2-(2-(4-methylphenyl)ethyl)-4-(4-methoxybenzylthiomethyl)-1,3-dioxolan-2-yl]methyl]imidazole,
1-[[2-(2-(4-methylphenyl)ethyl)-4-(4-n-butoxybenzylthiomethyl)-1,3-dioxolan-2-yl]methyl]imidazole, and
1-[[2-(2-(4-methylphenyl)ethyl)-4-(4-trifluoromethylbenzylthiomethyl)-1,3-dioxolan-2-yl]methyl]imidazole.

(I) Similarly, proceeding as in part (A) of this example, substituting the appropriate benzylthiols for 2-chlorobenzylthiol and substituting 1-[[2-(2-(4-t-butylphenyl)ethyl)-4-(methanesulfonyloxymethyl)-1,3-dioxolan-2-yl]methyl]imidazole for 1-[[2-(2-(4-chlorophenyl)ethyl-4-(methanesulfonyloxymethyl)-1,3-dioxolan-2-yl]methyl]imidazole the following compounds are prepared:

1-[[2-(2-(4-t-butylphenyl)ethyl)-4-(4-chlorobenzylthiomethyl)-1,3-dioxolan-2-yl]methyl]imidazole,
1-[[2-(2-(4-t-butylphenyl)ethyl)-4-(4-methylbenzylthiomethyl)-1,3-dioxolan-2-yl]methyl]imidazole, and
1-[[2-(2-(4-t-butylphenyl)ethyl)-4-(4-methoxybenzylthiomethyl)-1,3-dioxolan-2-yl]methyl]imidazole.

(J) Similarly, proceeding as in part (A) of this example, substituting 1-[[2-(2-(4-methoxyphenyl)ethyl)-4-(methanesulfonyloxymethyl)-1,3-dioxolan-2-yl]methyl]imidazole for 1-[[2-(2-(4-chlorophenyl)ethyl)4-(methanesulfonyloxymethyl)-1,3-dioxolan-2-yl]methyl]imidazole there is obtained 1-[[2-(2-(4-methoxyphenyl)ethyl)-4-(2-chlorobenzylthiomethyl)-1,3-dioxolan-2-yl]methyl]imidazole. By substituting the appropriate benzylthiols for 2-chlorobenzylthiol and substituting 1-[[2-(2-(4-methoxyphenyl)ethyl)-4-(methanesulfonyloxymethyl)-1,3-dioxolan-2-yl]methyl]imidazole for 1-[[2-(2-(4-chlorophenyl)ethyl)-4-(methanesulfonyloxymethyl)-1,3-dioxolan-2-yl]methyl]imidazole the following compounds are prepared:

1-[[2-(2-(4-methoxyphenyl)ethyl)-4-benzylthiomethyl-1,3-dioxolan-2-yl]methyl]imidazole,
1-[[2-(2-(4-methoxyphenyl)ethyl)-4-(3-chlorobenzylthiomethyl)-1,3-dioxolan-2-yl]methyl]imidazole,
1-[[2-(2-(4-methoxyphenyl)ethyl)-4-(4-chlorobenzylthiomethyl)-1,3-dioxolan-2-yl]methyl]imidazole,
1-[[2-(2-(4-methoxyphenyl)ethyl)-4-(4-bromobenzylthiomethyl)-1,3-dioxolan-2-yl]methyl]imidazole,
1-[[2-(2-(4-methoxyphenyl)ethyl)-4-(4-fluorobenzylthiomethyl)-1,3-dioxolan-2-yl]methyl]imidazole,
1-[[2-(2-(4-methoxyphenyl)ethyl)-4-(2,4-dichlorobenzylthiomethyl)-1,3-dioxolan-2-yl]methyl]imidazole,
1-[[2-(2-(4-methoxyphenyl)ethyl)-4-(2,5-dichlorobenzylthiomethyl)-1,3-dioxolan-2-yl]methyl]imidazole,
1-[[2-(2-(4-methoxyphenyl)ethyl)-4-(2,6-dichlorobenzylthiomethyl)-1,3-dioxolan-2-yl]methyl]imidazole,
1-[[2-(2-(4-methoxyphenyl)ethyl)-4-(2,4,6-trichlorobenzylthiomethyl)-1,3-dioxolan-2-yl]methyl]imidazole,
1-[[2-(2-(4-methoxyphenyl)ethyl)-4-(2-methylbenzylthiomethyl)-1,3-dioxolan-2-yl]methyl]imidazole,
1-[[2-(2-(4-methoxyphenyl)ethyl)-4-(3-methylbenzylthiomethyl)-1,3-dioxolan-2-yl]methyl]imidazole,
1-[[2-(2-(4-methoxyphenyl)ethyl)-4-(4-methylbenzylthiomethyl)-1,3-dioxolan-2-yl]methyl]imidazole,
1-[[2-(2-(4-methoxyphenyl)ethyl)-4-(2,4-dimethylbenzylthiomethyl)-1,3-dioxolan-2-yl]methyl]imidazole, 1-[[2-(2-(4-methoxyphenyl)ethyl)-4-(2,5-dimethyl-benzylthiomethyl)-1,3-dioxolan-2-yl]methyl]imidazole,
1-[[2-(2-(4-methoxyphenyl)ethyl)-4-(2,6-dimethyl-benzylthiomethyl)-1,3-dioxolan-2-yl]methyl]imidazole,
1-[[2-(2-(4-methoxyphenyl)ethyl)-4-(2,4,6-trimethyl-benzylthiomethyl)-1,3-dioxolan-2-yl]methyl]imidazole,
1-[[2-(2-(4-methoxyphenyl)ethyl)-4-(4-t-butylbenzyl-thiomethyl)-1,3-dioxolan-2-yl]methyl]imidazole,
1-[[2-(2-(4-methoxyphenyl)ethyl)-4-(4-phenylbenzyl-thiomethyl)-1,3-dioxolan-2-yl]methyl]imidazole,
1-[[2-(2-(4-methoxyphenyl)ethyl)-4-(4-(4-chloro-phenyl)benzylthiomethyl)-1,3-dioxolan-2-yl]methyl]imidazole,
1-[[2-(2-(4-methoxyphenyl)ethyl)-4-(4-(4-methyl-phenyl)benzylthiomethyl)-1,3-dioxolan-2-yl]methyl]-imidazole,
1-[[2-(2-(4-methoxyphenyl)ethyl)-4-(4-(4-methoxy-phenyl)benzylthiomethyl)-1,3-dioxolan-2-yl]methyl]-imidazole,
1-[[2-(2-(4-methoxyphenyl)ethyl)-4-(4-(4-trifluorome-thylphenyl)benzylthiomethyl)-1,3-dioxolan-2-yl]methyl]-imidazole,
1-[[2-(2-(4-methoxyphenyl)ethyl)-4-(2-methoxyben-zylthiomethyl)-1,3-dioxolan-2-yl]methyl]imidazole,
1-[[2-(2-(4-methoxyphenyl)ethyl)-4-(3-methoxyben-zylthiomethyl)-1,3-dioxolan-2-yl]methyl]imidazole,
1-[[2-(2-(4-methoxyphenyl)ethyl)-4-(4-methoxyben-zylthiomethyl)-1,3-dioxolan-2-yl]methyl]imidazole,
1-[[2-(2-(4-methoxyphenyl)ethyl)-4-(4-n-butoxyben-zylthiomethyl)-1,3-dioxolan-2-yl]methyl]imidazole, and
1-[[2-(2-(4-methoxyphenyl)ethyl)-4-(4-trifluorome-thylbenzylthiomethyl)-1,3-dioxolan-2-yl]methyl]-imidazole.

(K) Similarly, proceeding as in part (A) of this example, substituting the appropriate benzylthiols for 2-chlorobenzylthiol and substituting 1-[[2-(2-(4-n-butoxy-phenyl)ethyl-4-(methanesulfonyloxymethyl)-1,3-dioxo-lan-2-yl]methyl]imidazole for 1-[[2-(2-(4-chlorophenyl)ethyl)-4-(methanesulfonyloxymethyl)-1,3-dioxolan-2-yl]methyl]imidazole the following compounds are prepared:

1-[[2-(2-(4-n-butoxyphenyl)ethyl)-4-(4-chlorobenzyl-thiomethyl)-1,3-dioxolan-2-yl]methyl]imidazole,
1-[[2-(2-(4-n-butoxyphenyl)ethyl)-4-(4-methylbenzyl-thiomethyl)-1,3-dioxolan-2-yl]methyl]imidazole, and
1-[[2-(2-(4-n-butoxyphenyl)ethyl)-4-(4-methoxyben-zylthiomethyl)-1,3-dioxolan-2-yl]methyl]imidazole.

EXAMPLE 5

Nitric acid (70%; d-1.42) was added dropwise to a stirred solution of 2.0 g of cis-1-[[2-(2-(4-chlorophenyl)ethyl)-4-(2-chlorophenoxymethyl)-1,3-dioxolan-2-yl]methyl]imidazole in 30 ml of anhydrous ether until precipitation was complete. The product was filtered off, washed with ether, air dried, and recrystallized from ethyl acetate/acetone to yield 1-[[2-(2-(4-chloro-phenyl)ethyl)-4-(2-chlorophenoxymethyl)-1,3-dioxo-lan-2-yl]methyl]imidazole nitrate, m.p. 150°–152° C.

In similar manner, all compounds of Formula (I) prepared in accordance with Examples 1, 2, 3 and 4 in base form can be converted to their antimicrobial acid addition salts by treatment with the appropriate acid, for example, hydrochloric acid, hydrobromic acid, sulfuric acid, nitric acid, phosphoric acid, acetic acid, propionic acid, glycolic acid, lactic acid, pyruvic acid, oxalic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid or salicylic acid.

EXAMPLE 6

1-[[2-(2-(4-Chlorophenyl)ethyl)-4-(2-chlorophenox-ymethyl)-1,3-dioxolan-2-yl]methyl]imidazole nitrate (2.0 g) in 100 ml of dichloromethane was shaken with excess dilute potassium carbonate solution until the salt was completely dissolved. The organic layer was then separated, washed twice with water, dried over magnesium sulfate and evaporated to yield 1-[[2-(2-(4-chloro-phenyl)ethyl)-4-(2-chlorophenoxymethyl)-1,3-dioxo-lan-2-yl]methyl]imidazole as an oil.

In similar manner, the antimicrobial acid addition salts of all compounds of Formula (I) can be converted to the corresponding compounds in base form.

EXAMPLE 7

The following illustrates the preparation of representative pharmaceutical formulations which may be used for controlling fungi, bacteria and protozoa, utilizing an active compound such as a salt of 1-[[2-(2-(4-chloro-phenyl)ethyl)-4-(4-chlorophenylthiomethyl)-1,3-dioxo-lan-2-yl]methyl]imidazole.

| A. Topical Formulation | grams |
|---|---|
| Active compound | 0.2–2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | qs 100 |

All of the above ingredients, except water, are combined and heated at 60° C. with stirring. A sufficient quantity of water at 60° C. is then added with vigorous stirring to provide 100 g of the cream formulation which is then cooled to room temperature.

| B. Parenteral Formulation | |
|---|---|
| Active compound | 0.5 g |
| Propylene glycol | 20 g |
| Polyethylene glycol 400 | 20 g |
| Tween 80 | 1 g |
| 0.9 Saline solution qs | 100 ml |

The active compound is dissolved in propylene glycol, polyethylene glycol 400 and Tween 80. A sufficient quantity of 0.9% saline solution is then added with stirring to provide 100 ml of the I.V. solution which is filtered through a 0.2 micron membrane filter and packaged under sterile conditions.

| C. Oral Formulation | parts by weight |
| --- | --- |
| Active compound | 200 |
| Magnesium stearate | 3 |
| Starch | 30 |
| Lactose | 116 |
| PVP (polyvinylpyrrolidone) | 3 |

The above ingredients are combined and granulated using methanol as the solvent. The formulation is then dried and formed into tablets (containing 200 mg of active compound) with an appropriate tabletting machine.

I claim as my invention:

1. A compound of the formula:

$$R^1-CH_2CH_2-\underset{\underset{O\diagdown\diagup O}{C}}{\phantom{X}}-CH_2-N\diagup\diagdown N$$
$$\phantom{R^1-CH_2CH_2-C}|CH_2ZR^2$$

wherein:
Z is oxygen or sulfur;
$R^1$ is phenyl optionally substituted with one or more substituents selected from the group consisting of halo, lower alkyl, lower alkoxy and trifluoromethyl;
$R^2$ is phenyl or benzyl wherein the phenyl ring of $R^2$ is optionally substituted by one or more substituents selected from the group consisting of halo, lower alkyl, lower alkoxy and trifluoromethyl; or a phenyl optionally substituted by halo, lower alkyl, lower alkoxy and trifluoromethyl;
and the antimicrobial acid addition salts thereof.

2. A compound of claim 1 wherein Z is oxygen.

3. A compound of claim 2 wherein the substituents on $R^1$ are one or more halo, lower alkyl or lower alkoxy.

4. A compound of claim 3 wherein the substituent on $R^1$ is 4-halo, 4-lower alkyl or 4-lower alkoxy.

5. A compound of claim 4 wherein the substituent on $R^1$ is 4-chloro, 4-methyl or 4-methoxy.

6. A compound of claim 2 wherein $R^2$ is phenyl or benzyl wherein the phenyl ring of $R^2$ is optionally substituted by one substituent selected from the group consisting of halo, lower alkyl, lower alkoxy and 4-phenyl; or
two substituents selected from the group consisting of halo, methyl and methoxy; or
three or more substituents selected from the group consisting of chloro and methyl.

7. A compound of claim 6 wherein $R^2$ is optionally substituted phenyl.

8. A compound of claim 7 wherein $R^1$ is 4-chlorophenyl.

9. A compound of claim 8 wherein $R^2$ is phenyl, which is 1-[[2-(2-(4-chlorophenyl)ethyl)-4-phenoxymethyl-1,3-dioxolan-2-yl]methyl]imidazole and the antimicrobial acid addition salts thereof.

10. The compound of claim 8 wherein $R^2$ is 2-chlorophenyl which is 1-[[2-(2-(4-chlorophenyl)ethyl)-4-(2-chlorophenoxymethyl)-1,3-dioxolan-2-yl]methyl]imidazole and the antimicrobial acid addition salts thereof.

11. The compound of claim 8 wherein $R^2$ is 4-chlorophenyl which is 1-[[2-(2-(4-chlorophenyl)ethyl)-4-(4-chlorophenoxymethyl)-1,3-dioxolan-2-yl]methyl]imidazole and the antimicrobial acid addition salts thereof.

12. The compound of claim 8 wherein $R^2$ is 2,4-dichlorophenyl which is 1-[[2-(2-(4-chlorophenyl)ethyl)-4-(2,4-dichlorophenoxymethyl)-1,3-dioxolan-2-yl]methyl]imidazole and the antimicrobial acid addition salts thereof.

13. The compound of claim 8 wherein $R^2$ is 2,6-dichlorophenyl which is 1-[[2-(2-(4-chlorophenyl)ethyl)-4-(2,6-dichlorophenoxymethyl)-1,3-dioxolan-2-yl]methyl]imidazole and the antimicrobial acid addition salts thereof.

14. The compound of claim 8 wherein $R^2$ is 2,4,6-trichlorophenyl which is 1-[[2-(2-(4-chlorophenyl)ethyl-4-(2,4,6-trichlorophenoxymethyl)-1,3-dioxolan-2-yl]methyl]imidazole and the antimicrobial acid addition salts thereof.

15. The compound of claim 8 wherein $R^2$ is 2,6-dimethylphenyl which is 1-[[2-(2-(4-chlorophenyl)ethyl)-4-(2,6-dimethylphenoxymethyl)-1,3-dioxolan-2-yl]methyl]imidazole and antimicrobial acid addition salts thereof.

16. The compound of claim 8 wherein $R^2$ is 2,4,6-trimethylphenyl which is 1-[[2-(2-(4-chlorophenyl)ethyl)-4-(2,4,6-trimethylphenoxymethyl)-1,3-dioxolan-2-yl]methyl]imidazole and antimicrobial acid addition salts thereof.

17. The compound of claim 8 wherein $R^2$ is 4-phenylphenyl which is 1-[[2-(2-(4-chlorophenyl)ethyl)-4-(4-phenylphenoxymethyl)-1,3-dioxolan-2-yl]methyl]imidazole and antimicrobial acid addition salts thereof.

18. A compound of claim 6 wherein $R^2$ is optionally substituted benzyl.

19. A compound of claim 18 wherein $R^1$ is 4-chlorophenyl.

20. The compound of claim 19 wherein $R^2$ is benzyl which is 1-[[2-(2-(4-chlorophenyl)ethyl)-4-benzyloxymethyl-1,3-dioxolan-2-yl]methyl]imidazole and the antimicrobial acid addition salts thereof.

21. The compound of claim 19 wherein $R^2$ is 4-methoxybenzyl which is 1-[[2-(2-(4-chlorophenyl)ethyl)-4-(4-methoxybenzyloxymethyl)-1,3-dioxolan-2-yl]methyl]imidazole and the antimicrobial acid addition salts thereof.

22. The compound of claim 19 wherein $R^2$ is 2-methylbenzyl which is 1-[[2-(2-(4-chlorophenyl)ethyl)-4-(2-methylbenzyloxymethyl)-1,3-dioxolan-2-yl]methyl]imidazole and the antimicrobial acid addition salts thereof.

23. The compound of claim 19 wherein $R^2$ is 2,6-dimethylbenzyl which is 1-[[2-(2-(4-chlorophenyl)ethyl)-4-(2,6-dimethylbenzyloxymethyl)-1,3-dioxolan-2-yl]methyl]imidazole and the antimicrobial acid addition salts thereof.

24. The compound of claim 19 wherein $R^2$ is 4-chlorobenzyl which is 1-[[2-(2-(4-chlorophenyl)ethyl)-4-(4-chlorobenzyloxymethyl)-1,3-dioxolan-2-yl]methyl]imidazole and the antimicrobial acid addition salts thereof.

25. The compound of claim 19 wherein $R^2$ is 2-chlorobenzyl which is 1-[[2-(2-(4-chlorophenyl)ethyl)-4-(2-chlorobenzyloxymethyl)-1,3-dioxolan-2-yl]methyl]imidazole and the antimicrobial acid addition salts thereof.

26. The compound of claim 19 wherein $R^2$ is 4-fluorobenzyl which is 1-[[2-(2-(4-chlorophenyl)ethyl-4-(4-fluorobenzyloxymethyl)-1,3-dioxolan-2-yl]methyl- ]imidazole and the antimicrobial acid addition salts thereof.

27. The compound of claim 19 wherein $R^2$ is 2,4-dichlorobenzyl which is 1-[[2-(2-(4-chlorophenyl)ethyl)-4-(2,4-dichlorobenzyloxymethyl)-1,3-dioxolan-2-yl]methyl]imidazole and the antimicrobial acid addition salts thereof.

28. The compound of claim 1 wherein Z is sulfur.

29. A compound of claim 28 wherein the substituents on $R^1$ are one or more halo, lower alkyl or lower alkoxy.

30. A compound of claim 29 wherein the substituent on $R^1$ is 4-halo, 4-lower alkyl or 4-lower alkoxy.

31. A compound of claim 30 wherein the substituent on $R^1$ is 4-chloro, 4-methyl or 4-methoxy.

32. A compound of claim 28 wherein $R^2$ is phenyl or benzyl wherein the phenyl ring of $R^2$ is optionally substituted by
one substituent selected from the group consisting of halo, lower alkyl, lower alkoxy and 4-phenyl; or
two substituents selected from the group consisting of halo, methyl and methoxy; or
three or more substituents selected from the group consisting of chloro and methyl.

33. A compound of claim 32 wherein $R^2$ is optionally substituted phenyl.

34. A compound of claim 33 wherein $R^1$ is 4-chlorophenyl.

35. The compound of claim 34 wherein $R^2$ is phenyl which is 1-[[2-(2-(4-chlorophenyl)ethyl)-4-phenylthiomethyl-1,3-dioxolan-2-yl]methyl]imidazole and the antimicrobial acid addition salts thereof.

36. The compound of claim 34 wherein $R^2$ is 2-chlorophenyl which is 1-[[2-(2-(4-chlorophenyl)ethyl)-4-(2-chlorophenylthiomethyl)-1,3-dioxolan-2-yl]methyl]imidazole and the antimicrobial acid addition salts thereof.

37. The compound of claim 34 wherein $R^2$ is 3-chlorophenyl which is 1-[[2-(2-(4-chlorophenyl)ethyl)-4-(3-chlorophenylthiomethyl)-1,3-dioxolan-2-yl]methyl]imidazole and the antimicrobial acid addition salts thereof.

38. The compound of claim 34 wherein $R^2$ is 4-chlorophenyl which is 1-[[2-(2-(4-chlorophenyl)ethyl)-4-(4-chlorophenylthiomethyl)-1,3-dioxolan-2-yl]methyl]imidazole and the antimicrobial acid addition salts thereof.

39. The compound of claim 34 wherein $R^2$ is 2-methylphenyl which is 1-[[2-(2-(4-chlorophenyl)ethyl)-4-(2-methylphenylthiomethyl)-1,3-dioxolan-2-yl]methyl]imidazole and the antimicrobial acid addition salts thereof.

40. The compound of claim 34 wherein $R^2$ is 4-methylphenyl which is 1-[[2-(2-(4-chlorophenyl)ethyl)-4-(4-methylphenylthiomethyl)-1,3-dioxolan-2-yl]methyl]imidazole and the antimicrobial acid addition salts thereof.

41. The compound of claim 34 wherein $R^2$ is 2,5-dimethylphenyl which is 1-[[2-(2-(4-chlorophenyl)ethyl)-4-(2,5-dimethylphenylthiomethyl)-1,3-dioxolan-2-yl]methyl]imidazole and the antimicrobial acid addition salts thereof.

42. The compound of claim 34 wherein $R^2$ is 2,4,6-trimethylphenyl which is 1-[[2-(2-(4-chlorophenyl)ethyl)-4-(2,4,6-trimethylphenylthiomethyl)-1,3-dioxolan-2-yl]methyl]imidazole and the antimicrobial acid addition salts thereof.

43. The compound of claim 34 wherein $R^2$ is 2-methoxyphenyl which is 1-[[2-(2-(4-chlorophenyl)ethyl)-4-(2-methoxyphenylthiomethyl)-1,3-dioxolan-2-yl]methyl]imidazole and the antimicrobial acid addition salts thereof.

44. The compound of claim 34 wherein $R^2$ is 4-methoxyphenyl which is 1-[[2-(2-(4-chlorophenyl)ethyl)-4-(4-methoxyphenylthiomethyl)-1,3-dioxolan-2-yl]methyl]imidazole and the antimicrobial acid addition salts thereof.

45. The compound of claim 34 wherein $R^2$ is 2,6-dichlorophenyl which is 1-[[2-(2-(4-chlorophenyl)ethyl)-4-(2,6-dichlorophenylthiomethyl)-1,3-dioxolan-2-yl]methyl]imidazole and the antimicrobial acid addition salts thereof.

46. The compound of claim 34 wherein $R^2$ is 2,6-dimethylphenyl which is 1-[[2-(2-(4-chlorophenyl)ethyl)-4-(2,6-dimethylphenylthiomethyl)-1,3-dioxolan-2-yl]methyl]imidazole and the antimicrobial acid addition salts thereof.

47. The compound of claim 32 wherein $R^2$ is optionally substituted benzyl.

48. A compound of claim 33 wherein $R^1$ is 4-chlorophenyl.

49. The compound of claim 48 wherein $R^2$ is benzyl which is 1-[[2-(2-(4-chlorophenyl)ethyl)-4-benzylthiomethyl-1,3-dioxolan-2-yl]methyl]imidazole and the antimicrobial acid addition salts thereof.

50. The compound of claim 48 wherein $R^2$ is 4-chlorobenzyl which is 1-[[2-(2-(4-chlorophenyl)ethyl)-4-(4-chlorobenzylthiomethyl)-1,3-dioxolan-2-yl]methyl]imidazole and the antimicrobial acid addition salts thereof.

51. The compound of claim 48 wherein $R^2$ is 4-methoxybenzyl which is 1-[[2-(2-(4-chlorophenyl)ethyl)-4-(4-methoxybenzylthiomethyl)-1,3-dioxolan-2-yl]methyl]imidazole and the antimicrobial acid addition salts thereof.

52. The compound of claim 48 wherein $R^2$ is 4-methylbenzyl which is 1-[[2-(2-(4-chlorophenyl)ethyl)-4-(4-methylbenzylthiomethyl)-1,3-dioxolan-2-yl]methyl]imidazole and the antimicrobial acid addition salts thereof.

53. The compound of claim 48 wherein $R^2$ is 2-chlorobenzyl which is 1-[[2-(2-(4-chlorophenyl)ethyl)-4-(2-chlorobenzylthiomethyl)-1,3-dioxolan-2-yl]methyl]imidazole and the antimicrobial acid addition salts thereof.

54. A composition useful for inhibiting the growth of fungi, bacteria or protozoa which comprises an effective amount of a compound of the formula

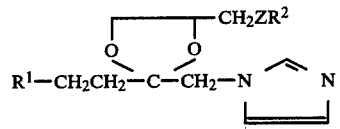

in admixture with a suitable carrier;
wherein:
Z is oxygen or sulfur;
$R^1$ is phenyl optionally substituted with one or more substituents selected from the group consisting of halo, lower alkyl, lower alkoxy and trifluoromethyl;
$R^2$ is phenyl or benzyl wherein the phenyl ring of $R^2$ is optionally substituted by one or more substituents selected from the group consisting of halo, lower alkyl, lower alkoxy and trifluoromethyl; or a phenyl optionally substituted by halo, lower alkyl, lower alkoxy and trifluoromethyl;

or an antimicrobial acid addition salt thereof.

55. The composition of claim 54 suitable for pharmaceutical use wherein the carrier is a pharmaceutically acceptabe, non-toxic carrier.

56. A method of inhibiting the growth of fungi, bacteria or protozoa which comprises applying to a host object containing, or subject to attack by, fungi, bacteria or protozoa an effective amount of a compound of the formula

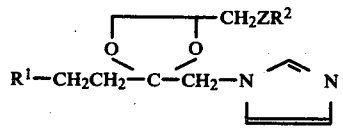

wherein:
Z is oxygen or sulfur;
R¹ is phenyl optionally substituted with one or more substituents selected from the group consisting of halo, lower alkyl, lower alkoxy and trifluoromethyl;
R² is phenyl or benzyl wherein the phenyl ring of R² is optionally substituted by one or more substituents selected from the group consisting of halo, lower alkyl, lower alkoxy and trifluoromethyl; or a phenyl optionally substituted by halo, lower alkyl, lower alkoxy or trifluoromethyl;
or a composition containing same as an active ingredient.

* * * * *